US005840851A

United States Patent [19]

Plomer et al.

[11] Patent Number: 5,840,851
[45] Date of Patent: *Nov. 24, 1998

[54] PURIFICATION OF HEMOGLOBIN

[76] Inventors: J. Jeffrey Plomer, 12636 Grove St., Broomfield, Colo. 80020; James R. Ryland, 946 St. Andrews La., Louisville, Colo. 80027; Maura-Ann H. Matthews, 3100 N. Broadway, Apt. 205, Boulder, Colo. 80304; David W. Traylor, 4045 Field Dr., Wheat Ridge, Colo. 80033; Erin E. Milne, 2206 Sunridge Cir., Broomfield, Colo. 80020; Steven L. Durfee, 6739 Montview Blvd., Denver, Colo. 80207; Antony J. Mathews, 673 W. Locust Ct., Louisville, Colo. 80027; Justinian O. Neway, 3197 Nelson Rd., Longmont, Colo. 80503

[*] Notice: The terminal 12 months of this patent has been disclaimed.

[21] Appl. No.: 438,511

[22] Filed: May 10, 1995

Related U.S. Application Data

[63] Continuation-in-part of Ser. No. 339,304, Nov. 14, 1994, abandoned, which is a continuation-in-part of Ser. No. 97,273, Jul. 23, 1993, abandoned.

[51] Int. Cl.[6] .............................. C07K 1/22; C07K 1/18
[52] U.S. Cl. .................... 530/385; 530/412; 530/413; 530/416; 514/6
[58] Field of Search ...................... 514/6; 530/413, 530/412, 416, 385

[56] References Cited

U.S. PATENT DOCUMENTS

| | | | |
|---|---|---|---|
| 4,301,144 | 11/1981 | Iwashita et al. | 514/6 |
| 4,321,259 | 3/1982 | Nicolau et al. | 424/93.73 |
| 4,336,248 | 6/1982 | Bonhard | 530/354 |
| 4,377,512 | 3/1983 | Ajisaka et al. | 530/385 |
| 4,401,652 | 8/1983 | Simmonds et al. | 424/101 |
| 4,412,989 | 11/1983 | Iwashita et al. | 514/762 |
| 4,439,357 | 3/1984 | Bonhard et al. | 260/112 B |
| 4,473,494 | 9/1984 | Tye | 260/112 B |
| 4,473,563 | 9/1984 | Nicolau et al. | 514/78 |
| 4,526,715 | 7/1985 | Klothe | 260/112 B |
| 4,598,064 | 7/1986 | Walder | 514/6 |
| 4,600,531 | 7/1986 | Walder | 530/385 |
| 4,650,786 | 3/1987 | Wong | 514/6 |
| 4,670,417 | 6/1987 | Iwasaki et al. | 514/6 |
| 4,710,488 | 12/1987 | Wong | 514/6 |
| 4,723,000 | 2/1988 | Georgiades et al. | 530/416 |
| 4,831,012 | 5/1989 | Estep | 514/6 |
| 4,857,636 | 8/1989 | Hsia | 530/385 |
| 4,861,867 | 8/1989 | Estep | 530/385 |
| 4,952,684 | 8/1990 | Yalpani et al. | 536/18.7 |
| 4,975,246 | 12/1990 | Charm | 422/21 |
| 5,028,588 | 7/1991 | Hoffman et al. | 514/6 |
| 5,077,388 | 12/1991 | Tang et al. | 530/351 |
| 5,084,558 | 1/1992 | Rausch et al. | 530/385 |
| 5,115,100 | 5/1992 | Wu et al. | 530/385 |
| 5,136,026 | 8/1992 | Romisch et al. | 530/416 |
| 5,169,936 | 12/1992 | Staples et al. | 530/380 |
| 5,194,590 | 3/1993 | Sehgal et al. | 530/385 |
| 5,264,555 | 11/1993 | Shorr et al. | 530/385 |
| 5,310,648 | 5/1994 | Arnold et al. | 435/5 |
| 5,510,247 | 4/1996 | Komives et al. | 435/41 |
| 5,545,328 | 8/1996 | Pliura et al. | 210/635 |

FOREIGN PATENT DOCUMENTS

| | | |
|---|---|---|
| 0073888 | 6/1982 | European Pat. Off. . |
| 0132178 | 1/1985 | European Pat. Off. . |
| 0231236 | 8/1987 | European Pat. Off. . |
| 0277289 | 8/1988 | European Pat. Off. . |
| 8700177 | 1/1987 | WIPO . |
| 8906969 | 8/1989 | WIPO . |
| 8912456 | 12/1989 | WIPO . |
| 9100290 | 6/1990 | WIPO . |
| 9012803 | 11/1990 | WIPO . |
| 9013645 | 11/1990 | WIPO . |
| 9116349 | 10/1991 | WIPO . |
| 9211283 | 7/1992 | WIPO . |
| 9222646 | 12/1992 | WIPO . |
| 9308831 | 5/1993 | WIPO . |
| 9514038 | 5/1995 | WIPO . |

OTHER PUBLICATIONS

Kato et al., 'High–performance metal chelate affinity chromatography of proteins', Journal of Cromatography, 354, pp. 511–517, 1986.

Fogh–Andersen, N. et Al/Diode–Array Spectrophotometry for Simultaneous Measurement of Hemoglobin Pigments/Clinica Chimica Acta/(1987) 166: 283–289.

Beguin, P. et Al/Identification of the Endoglucanase Encoded by the celB Gene of Clostridium Thermocellum/Biochimie/(1983) 65: 495–500.

Figueroa, A. et Al/High–Performance Immobilized–Metal Affinity Chromatography of Proteins on Iminodiacetic Acid Silica–Based Bonded Phases/J. of Chromatography/(1986) 371: 335–352.

Zwart, A. et Al/Multicomponent Analysis of Hemoglobin Derivatives with a Revesed–Optics Spectrophotometer/Clin. Chem./(1984) 30: 373–379.

HSIA & SWEE ER/Purification of Stroma–Free Haemoglobin by ATP—Agarose Affinity Chromatography/J. of Chromatography/(1986) 374:143–148.

ESTEP et al/The Purification Hemoglobin Solutions by Heating/Progress in Clinical and Biological Research/The Red Cell Seventh Ann Arbor Conference/(1989) 319: 325–338/ed. George J. Brewer/Alan R. Liss, Inc. New York.

(List continued on next page.)

Primary Examiner—Cecilia J. Tsang
Assistant Examiner—Anish Gupta

[57] ABSTRACT

The present invention generally relates to methods for purifying hemoglobin solutions and to hemoglobin solutions obtained by the methods. In one aspect, such methods include removing contaminants in crude hemoglobin-containing lysates with heat treatment. In a further aspect, the present invention provides methods for producing substantially purified hemoglobin solutions using immobilized metal affinity chromatography, optionally following by anion exchange chromatography.

51 Claims, 2 Drawing Sheets

OTHER PUBLICATIONS

Van Assendelft, O.W. & ijlstra, W.G./Extinction Coefficients for use in Equations for the Spectrophotometric Analysis of Haemoglobin Mixtures/Anal. Biochem./(1975)/69: 43–48.

Antonini, E. & Brunori, M./Hemoglobin and Myoglobin in their Reactions with Ligands/Frontiers of Biology/Structure– Function Relationships in Hemoglobin and Myoglobin/(1971)/21: Chapter 13/348–380/North–Holland Publishing Co./Ed. A. Neuberger & E.L. Tatum.

Antonini, E. & Brunori, M./Hemoglobin and Myoglobin in their Reactions with Ligands/Frontiers of Biologyspecific aspects of the Reactions of Hemoglobin with Ligands/(1971)/21: Chapter 10/235–285/North–Holland Publishing Co./Ed. A. Neuberger & E.L. Tatum.

Benesch, R.E. et al./Equations for the Spectrophotometric Analysis of Hemoglobin Mixtures/Anal. Biochem./(1973)/55: 245–248.

Chang, T.M.S./Modified Hemoglobin: Endotoxin and Safety Studies/Biomat., Art. Cells, Art. Org.,/(1990)/18(2): VII–VIII.

Collison, H.A. et al./Determination of Carbon Monoxide in Blood by Gas Chromatography/Clin. Chem./(1968)/14(2): 162–171.

Commins, B.T. & Lawther, P.J./A Sensitive Method for the Determination of Carboxy–Haemoglobin in a Finger Prick Sample of Blood/Brit. J. Industr. Med./(1965)/22: 139–143.

Darnall, D.W. et al./Selective Recovery of Gold and Other Metal Ions from an Algal Biomass/Environ. Sci. Technol./(1986) 20: 206–208.

Di Iorio, E.E./Preparation of Derivatives of Ferrous and Ferric Hemoglobin/Methods in Enzymology/(1981)/76: 57–72/Academic Press/ Ed. E. Antonini/L. Rossi–Bernardi, E. Chiancone.

Evylyn, K.A. & Malloy, H.T./Microdetermination of Oxyhemoglobin, Methemoglobin, and Sulfhemoglobin, in a Single Sample of Blood/The J. of Bio. Chem./(1938)/126: 655–662.

Figura, P. & McDuffie, B./Characterization of the Calcium Form of Chelex–100 for Trace Metals Studies/Analytical Chemistry/(1977)/49(13): 1950–1953.

Heindorff, K. et al./Genetic Toxicology of Ethylenediaminetetraacetic Acid (EDTA)/Mutation Research/(1983)/115: 149–173.

Johansson, M.–B. & Wollmer, P./Measurement of Carboxyhaemoglobin by Spectrophoto–Metry and Gas Chromatography/Clinical Physiology/(1989)/9: 581–586.

Kato, Y. et al./High–Performance Metal Chelate Affinity Chromatography of Proteins/J. of Chromatography/(1986) 354: 511–517.

Kikugawa, K. et al./Factors Influencing the Autoxidation of Hemoglobin A/Chem. Pharm. Bull./(1981)/29(5): 1382–1389.

Liebhaber, S.A. et al./Cloning and Complete Nucleotide Sequence of Human 5'–α–Globin Gene/PNAS/(1980)/77(12): 7054–7058.

Marotta, C.A. et al./Human β–Globin Messenger RNA/J. of Biological Chem./(1977)/252: 5040–5053.

Marshall, T. et al./Trace Element Analyses of Diaspirin Cross–Linked Hemoglobin Solutions/Blood Substitutes and Oxygen Carriers/(1993)/Marcel Dekker, Inc./Ed. Chang. T.M.S.

Moyers, E.M. & Fritz, J.S./Preparation and Analytical Applications of a Propylenedia–Minetetraacetic Acid Resin/Anal. Chem./(1977)/49(3)/418–423.

Rabiner, S.F. et al/Evaluation of a Stroma–Free Hemoglobin Solution for use as a Plasma Expander/J. Experimental Med./(1967)126: 1127–1142.

Rietschel, E.T. & Brade, H./Bacterial Endotoxins/Scientific American/(1992)/267: 54–61.

Rodkey, F.L. et al./Spectrophotometric Measurement of Carboxyhemoglobin and Methe–Moglobin in Blood/Clin. Chem./(1979)/25(8): 1388–1393.

Small, K.A. et al/A Rapid Method for Simultaneous Measurement of Carboxy–and Methe–Moglobin in Blood/J. of Applied Physiology/(1971)/31(1): 154–160.

Suffredini, A.F. et al/The Cardiovascular Response of Normal Humans to the Admini–stration of Endotoxin/The New England J. of Med./(1989)/321(5): 280–287.

Tanaka, T. et al/Cloning of 3–Isopropylmalate Dehydrogenase Gene of an Extreme Themo–Phile Purification of the Gene Product/Biochemistry/(1981)/89: 677–682.

Tentori, L. & Salvati, A.M./Hemoglobinometry in Human Blood/Methods in Inzymology/(1981)/76: 707–715/Ed. Antonini, E; Rossi–Bernardi, L.; Chiancone, E./Academic Press Tsukagoshi, N. et al/Cloning and Expression of a Thermophilic α–Amylase Gene from Bacillus Stearothermophilus in Escherichia Coli/Mol. Gen Genet/(1984)/193: 58–63.

Vernon, P./Novel Ion Exchangers–The Preparation and Properties of Chelating ion Ex–Change Resins/Chem. & Industry/(1977)/15: 634–637.

White, C.T. et al/Synergistic Toxicity of Endotoxin and Hemoglobin/J. Lab. Clin. Med./(1986) 108(2): 132–137.

Wuenschell, G.E. et al/Aqueous Two–Phrase Metal Affinity Extraction of Heme Proteins/Bioprocess Engineering/(1990)/5: 199–202.

Yip, T–T. et al/Evaluation of the Interaction of Peptides with Cu(II), Ni(II), and Zn(II) by High–Performance Immobilized Metal Ion Affinity Chromatography/Anal. Biochem./(1989)/183: 159–171.

Zijlstra, W.G. et al/Absorption Spectra of Human Fetal and Adult Oxyhemoglobin, De–Oxyhemoglobin, Carboxyhemoglobin, and Methemoglobin/Clin. Chem./(1991)/37(9): 1633–1638.

Chemical Engineering Handbook/5th Edition/(1973)/6/29–6/32/McGraw W–Hill/New York/Ed. R.H. Perry/C.H. Chilton.

Lindeberg, G. et al/Purification of Synthetic Peptides/Int.J. Peptide Protein Res./(1991) 38: 253–259.

Figueroa, A. et al./High–Performance Immobilized–Metal Affinity Chromatography of Proteins on Iminodiacetic Acid Silica–Based Bonded Phases/J. of Chromatography/(1986) 371: 335–352.

Leach, C.N., et al/Serum Nickelconcentrations in Patients Wit Unstable Angina and Myocardial Infarction/Ann. Clin. Lab. Sci./(1984), 14(5), 414–415.

Sarkar, B./Nickel Metablolism/Nickel in the Human Environment/Pub: Int. Agency for Res. on Cancer, Lyon, France/(1984), 367–384.

Leach, C.A. & Sunderman, W./Hypernickelemia Induced by Nickel Contamination of Radiographic Contrast Media/Ann. Clin. Lab. Sci./(1986), 16(4), 327–328.

Haner, M. et al/Synthesis of Affinity–Label Chelates: A Novel Synthetic Method of Coupling Ethylenediaminetetraacetic Acid to Amine Functional Groups/Arch. of Biochem. & Biophys./(1984), 231(2), 477–486.

Haner, M. et al/Synthesis of a New Chelating Gel: Removal of $Ca^{2+}$ Ions from Parval–Bumin/Anal. Biochemistry/(1984), 138, 229–234.

Kilburn, K.H. et al/Cross–Shift and Chronic Effects of Stainless–Steel Welding Related to Internal Dosimetry of Chromium and Nickel/AM. J. of Indust. Med./(1990), 17, 607–615.

Knight, J.A. et al/Pulmonary Bronchoal Veolar Hyperplasia in Rats After Protracted Parenteral Injections of Nickel Chloride./Ann. Clin. & Lab. Sci./(1987), 17(4), 275.

Knight, J.A. et al/Pathological Reactions in Lung, Liver, Thymus, and Spleen of Rats After Subacute Parenteral Administration of Nickel Sulfate/Ann. of Clin. & Lab. Sci./(1991), 21(4), 275–283.

Blackburn, K. & Highsmith, R.F./Nickel Inhibits Endothelin–Induced Contractions of Vascular Smooth Muscle/AM. J. of Physiol./(1990), 258, C1025–C1030.

Lucassen, M. & Sarkar, B./Nickel (II)–Binding Constituents of Human Blood Serum/J. of Toxicology & Environmental Health/(1979), 5, 897–905.

Marshall, T. et al/Trace Element Analyses of Diaspirin Cross–Linked Hemoglobin Solutions/Blood Substitutes and Oxygen Carriers/Ed.: T.M.S. Chang/Marcel Dekker, Inc., NY/(1993), 267–270.

Louria, D.B. et al/The Human Toxicity of Certain Trace Elements/Ann. Internal Med./(1972), 76, 307–319.

Fratantoni, J.C./Points to Consider in the Safety Evaluation of Hemoglobin–Based Oxygen Carriers/Transfusion/(1991), 31(4), 369–371.

Gramm, H.J. et al/Spurenelementgehalt in Losungen Zur Parenteralen Ernahrung und Blutderivaten/Infusionstherapie/(1987), 14, 290–294.

Berner, Y.N. et al/Selected Ultratratrace Elements in Total Parenteral Nutrition Solutions/AM. J. Clin. Nutr./(1989), 50, 1079–1083.

Leach, C.A. & Sunderman, F.W./Hypernickelemia Following Coronary Arteriography, Caused by Nickel in the Radiographic Contrast Medium/Ann. Clin. & Lab. Sci./(1987), 17(3), 137–144.

Nielsen, F.H./Fluoride, Vanadium, Nickel, Arsenic, and Silicon in Total Parenteral Nutrition/(1984), 60(2), 177–195.

Gross, P. et al/Experimental Asbestosis/The Development of Lung Cancer in Rats with Pulmonary Deposits of Chrysotile Asbestos Dust/Arch. Envir. Health/(1967), 15, 343–355.

Koppel, C. & Baudisch, H./Inadvertent Metal Loading of Critically Ill Patients with Acute Renal Failure by Human Albumin Solution Infusion Therapy/Clin. Tox./(1988), 26(5&6), 337–356.

Holti, G./Immediate and Arthus–Type Hypersensitivity to Nickel/Clin. Allergy/ (1974), 4, 437–438.

O'Sullivan, W.J./Stability Constants of Metal Complexes/ Data for Biochemical Research/ (1969), Oxford University Press, NY, Ed. R.M.C. Dawson, D.C. Elliott, W.H. Elliott, K.M. Jones, Chapter 17, pp. 423–434.

Callan, W.M. & Sunderman, F.W./Species Variations in Binding of $^{63}$NI(II) by Serum Albumin/ Res. Comm. Chem. Path. Pharm./(1973), 5(2), 459–471.

Sunderman, F.W./Potential Toxicity from Nickel Contamination of Intravenous Fluids/ Ann. of Clin. & Lab. Sci./ (1983), 13(1), 1–4.

Fisher, A.A./Nickel—The Ubiquitous Contact Allergen Possible Significance of its Presence in Food, Water, Urine, Hair, and Infusion Fluids/Cur. Contact News/(1978), 22(5), 544–550.

Rubanyi, G. & Balogh, I./Effect of Nickel on Uterine Contraction and Ultrastructure in the Rat/AM. J. Obstet. Gynecol./(1982), 142(8), 1016–1020.

Serda, R.E. & Henzl, M.T./Metal Ion–Binding Properties of a Avian Thymic Hormone/The J. of Biological Chemistry/ (1991), 266(11), 7291–7299.

Sunderman, F.W./A Pilgrimage into the Archives of Nickel Toxicology/Ann. of Clin. & Lab. Sci./(1989), 19(1), 1–16.

Tabata, M. & Sarkar, B./Specific Nickel (II)–Transfer Process Between the Native Sequence Peptide Representing the Nickel (II)–Transport Site of Human Serum Albumin and L–Histidine/J. Inorganic Biochem./(1992), 45, 93–104.

Vernon, F./The Preparation and Properties of Chelating Ion Exchange Resins/Chemistry and Industry/(1977), 15, 634–637.

Morgan, W.T./Human Serum Histidine–Rich Glycoprotein/ I. Interactions with Heme, Metal Ions and Organic Ligands/ Biochim. et Biophys. Acta/(1978), 533, 319–333.

Darnall, D.W. et al/Selective Recovery of Gold and Other Metal Ions from an Algal Biomass/Environ. Sci. Technol./ (1986), 20, 206–208.

Edoute, Y. et al/Nickel Chloride Inhibits Metabolic Coronary Vasodilation in Isolated Rat Hearts/Federation Proceedings/(1986), 45(3), 1410.

Figura, P. & McDuffle, B./Characterization of the Calcium Form of Chelex–100 for Trace Metal Studies/Analytical Chemistry/(1977), 49(13), 1950–1953.

Rubanyi, G. et al/Nickel is Released from the Ischemic Myocardium and Contracts Coronary Vessels by a Ca–Dependent Mechanism/J. Mol. & Cell. Card./(1981), 13, 1023–1026.

Rubanyi, G. & Kovach, A.G.B./Coronary Vasoconstriction Induced by Endogenous Nickel Release in Various Cardivascular Diseases/Ann. Clin. Lab. Sci./(1981), 11(1), 93.

Oskarsson, A. et al/Effects of Cobalt Chloride, Nickel Chloride, and Nickel Subsulfide and Upon Erythropoiesis in Rats/Ann. of Clin. & Lab Sci./(1981), 11(2), 165–172.

Novelli, E.L.B. et al/Influence of Nickel Chloride on Bone Marrow of Iron–Defiecient Rats/ Bol. Estud. Med. Biol. Mex./(1988), 36, 35–42.

Moyers, E.M. & Fritz, J.S./Preparation and Analytical Applications of a Propylenediaminetetraacetic Acid Resin/ Anal. Chem./(1977), 49(3), 418–423.

Sharma, B. L. et al./Chelation in Metal Intoxication. XIX. α–Mercapto–β–Aryl Acrylic Acid as Antidotes to Nickel and Lead Toxicity/J. of Applied Toxicology/(1986)/6(4) 253–257.

PURIFICATION OF HEMOGLOBIN

CROSS-REFERENCES TO RELATED APPLICATIONS

This application is a continuation-in-part of application Ser. No. 08/339,304, filed Nov. 14, 1994, now abandoned which is a continuation-in-part of application Ser. No. Ser. No. 08/097,273, filed Jul. 23, 1993, now abandoned, both incorporated herein by reference in their entirety.

FIELD OF THE INVENTION

This invention relates to methods for the purification of hemoglobin.

BACKGROUND OF THE INVENTION

Severe blood loss requires both replacement of the volume of fluid that is lost and replacement of oxygen carrying capacity. This is typically accomplished by transfusing red blood cells, either as packed RBC's or as units of whole blood. However, it is not always possible, practical or desirable to transfuse a patient with donated blood. In situations where human blood is not available, volume can be replaced utilizing plasma expanders such as colloid and crystalloid solutions. However, none of the volume replacement therapies currently approved for human use can transport oxygen. In these situations, a red blood cell substitute such as a hemoglobin solution that transports oxygen is desirable. Administration of a hemoglobin solution can increase and/or maintain plasma volume and decrease blood viscosity in the same manner as conventional plasma expanders, but, in addition, a hemoglobin-based red blood cell substitute should be able to support adequate transport of oxygen from the lungs to peripheral tissues.

The only current therapy with the capability of increasing plasma volume as well as transporting oxygen is human blood transfusion. Human blood transfusions, however, are associated with many risks and limitations, such as, for example:

1) Infectious disease transmission (i.e., human immunodeficiency virus (HIV), non-A and non-B hepatitis, hepatitis B, *Yersinia enterocolitica,* cytomegalovirus, human T-cell leukemia virus 1 and 2)
2) Immunologic reaction (i.e., transfusion reactions, immunosuppresion, graft versus host reaction)
3) Not universally compatible
4) Limited availability
5) Limited stability (shelf life of 42 days or less; cannot be frozen)

The oxygen carrying component of the red blood cell is the protein molecule hemoglobin. Human hemoglobin Ao (also known as naturally occurring or native hemoglobin) is a tetrameric protein molecule composed of two identical alpha globin subunits ($\alpha_1, \alpha_2$) and two identical beta globin subunits ($\beta_1, \beta_2$). In a hemoglobin tetramer, each alpha globin is associated with a beta globin to form two stable alpha/beta dimers, which in turn associate to form the tetramer. The subunits are noncovalently associated through Van der Waals forces, hydrogen bonds and salt bridges. A heme molecule is incorporated into each of the alpha and beta globins. Heme is a large organic molecule coordinated around an iron atom. Heme that does not contain iron is called protoporphyrin IX (PIX) and is non-functional (cannot bind a ligand). Protoporphyrin IX can occur in one or more of the hemoglobin subunits, rendering that particular subunit unable to bind or release a ligand.

In the deoxygenated ("deoxy", or "T" for "tense") state, the four subunits form a tetrahedron. During ligand binding, the $\alpha_1\beta_1$ and $\alpha_2\beta_2$ interfaces remain relatively fixed while the $\alpha_1\beta_2$ and $\alpha_2\beta_1$ interfaces exhibit considerable movement. When the hemoglobin molecule is oxygenated, the intersubunit distances are increased relative to the deoxygenated distances, and the molecule assumes the "R" configuration (relaxed state) which is the predominant form of the molecule when a ligand is bound to the heme.

Genetic engineering techniques have allowed the expression of heterologous proteins in a number of biological expression systems, such as insect cells, plant cells, transgenic cells, yeast systems and bacterial systems. Because the sequences of alpha and beta globin of hemoglobin are known, and efficient expression criteria have been determined, it is possible that any suitable biological protein expression system can be utilized to produce large quantities of recombinant hemoglobin. Indeed, hemoglobin has been expressed in a number of biological systems, including bacteria (Hoffman et al., WO 90/13645), yeast (De Angelo et al., WO 93/08831 and WO 91/16349; Hoffman et al., WO 90/13645) and transgenic mammals (Logan et al., WO 92/22646; Townes, T. M and McCune, S. L., WO 92/11283). Although heterologous expression of hemoglobin in these systems can be achieved at high levels, purification of the final product to the level of purity required for high volume pharmaceutical administration of hemoglobin remains difficult.

Nevertheless, hemoglobin has been purified from some of these expression systems as well as from outdated human and mammalian red blood cells. Purification of hemoglobin generally requires at least some lytic step to liberate the hemoglobin from the cellular matrix, a low resolution fractionation step to remove contaminating soluble and insoluble proteins, lipids, membranes, etc. (e.g., filtration, centrifugation, pH dependent precipitation, heating) followed by some form of chromatographic final purification steps. For example, hemoglobin has been isolated and purified from outdated human red blood cells by hemolysis of erythrocytes followed by cation exchange chromatography (Bonhard, K., et al., U.S. Pat. No. 4,439,357), anion exchange chromatography (Tayot, J. L. et al., EP Publication 0 132 178; Shorr, et al., U.S. Pat. No. 5,264,555), affinity chromatography (Hsia, J. C., EP Patent 0 231 236 B1), filtering through microporous membranes (Rabiner, S. F. et al., *J. Exp. Med.* 126: 1127–1142, 1967), slowly heating a deoxygenated solution of semi-purified hemoglobin to precipitate residual contaminants (Estep, T. N., PCT application PCT/US89/014890, Estep, T. N., U.S. Pat. No. 4,861,867), precipitating contaminants by the addition of polyvalent ions and polysulfates (Simmonds, R. S and Owen, W. P., U.S. Pat. No. 4,401,652) or precipitating the hemoglobin itself with zinc followed by resuspension (Tye, R. W., U.S. Pat. No. 4,473,494). Hemoglobin has also been purified from other sources, e.g. bovine blood, and treated by any of the methods above or by microporous filtration, ultrafiltration and finally ion exchange chromatography (Rausch, C. W. and Feola, M., EP 0 277 289 B1, Rausch, C. W. and Feola, M., U.S. Pat. No. 5,084,558) or by ultrafiltration alone (Kothe, N. and Eichentopf, B., U.S. Pat. No. 4,562,715). Recombinant hemoglobins produced in transgenic animals have been purified by chromatofocusing (Townes, T. M. and McCune, S. L., PCT application PCT/US/09624).

These techniques, however, are generally associated with purification of hemoglobin from starting materials that are substantially free of contaminants such as bacterial contaminants. As a result, these purification techniques are not generally applicable for the purification of hemoglobin from any source, and are especially not suited for the purification of material from recombinant sources such as yeast and bacterial cells. Purification of hemoglobin contaminated with bacterial contaminants, such as recombinant hemoglobin produced in microbial expression systems poses unique problems due to the extraordinarily large contamination of the expressed protein with microbial proteins, cellular components, and especially bacterial lipopolysaccharides (endotoxins) upon lysis of the microbial cells. All these non-hemoglobin components can elicit pyrogenic responses upon administration in even minute amounts to mammals, and may even lead to sepsis and death (Rietschel, E. T. and Brade, H. *Scientific American* 267: 54–61, 1992; Suffredini, A. F. et al., *New Eng. J. Med.* 321: 280–287, 1989). The necessity for removal of any bacterial contaminants from hemoglobin is even more pressing in light of the observation that hemoglobin and endotoxin co-administration result in an observed enhancement of the lethality of endotoxin compared to the toxicity of endotoxin alone (White, C. T. et al., *J. Lab. Clin. Med.* 108: 132–137, 1986; Chang, T. M. S. et al., *Biomat., Art. Cells, Art. Org.,* 18(2): vii–viii, 1990).

The concern with contamination from bacterial components is clearly illustrated in U.S. Pat. No. 5,084,558 to C. W. Rausch and M. Feola. They state that the starting material (bovine erythrocytes) used for extra or ultrapure hemoglobin blood substitute solutions must be relatively free of bacterial contamination and note that "Avoiding the introduction of bacteria and the maintenance of endotoxin-free or low endotoxin level material is important" (column 13, lines 29–31). They further state that "If the endotoxin level [of the blood] is higher than 6–7 EU [Endotoxin Units] per ml the blood is discarded" (column 13, lines 57–58). Starting levels of somewhat greater than 250 EU/ml have been removed utilizing chelation in the presence of a detergent (Römisch, J. and Heimburger, N., U.S. Pat. No. 5,136,026). However, when heterologous proteins are expressed in microbial systems, especially bacterial systems, and the cells are lysed to release the expressed protein, the endotoxin contamination of the resultant lysate is millions of EU per ml. Thus any purification technique that would be utilized for the purification of hemoglobin expressed in microbial systems must be able to reduce enormous quantities of endotoxin contamination to low, pharmaceutically acceptable levels. Stringent purification of hemoglobin is required for pharmaceutical uses of hemoglobin, particularly large volume uses of hemoglobin such as for blood substitutes. This is due both to the potentiation of possible contaminant effects by direct interaction with hemoglobin as discussed above, and the fact that although a contaminant may be a relatively low levels in a hemoglobin solution (for example, parts per million or less), a large volume of a hemoglobin solution might be administered to a patient. Thus the high volumes of hemoglobin that could be administered to a patient would result in the administration of a high absolute quantity of a contaminant.

A number of purification systems have been developed to reduce the amount of contaminating bacterial components in protein solutions. For example, heating of bacterial cell lysates, particularly *E. coli* lysates, is a common technique utilized in the purification of proteins derived from recombinant technology. However, heating of the material in solution after lysis of bacterial cells has generally been restricted to purification of known heat-stable proteins. This technique exploits the differences in thermal stability between most bacterial proteins and the heterologous protein. For example, Tanaka and co-workers (Tanaka et al., *Biochemistry* 89: 677–682, 1981) expressed 3-isopropylmalate dehydrogenase from a thermophilic bacterium in *E. coli*, and purified this enzyme by heating the crude lysate for 10 minutes at 70° C. They note that this was a simple and effective procedure for rapidly purifying protein, and further state that "the enzymes of extreme thermophiles are stable in conditions where most of the proteins of *E. coli* cells used as host are heat denatured and precipitated . . . these observations suggest that any thermophilic enzyme can be purified with relative ease by cloning the genes in question into *E. coli*. Heat purification of protein was also used by Beguin and others in 1983 (Beguin, et al. *Biochimie* 65: 495–500, 1983) to purify another heat stable protein (endogluconase B) by a heat treatment at 60° C. for 15 minutes.

Tsukagoshi and co-workers (Tsukagoshi et al., *Mol. Gen. Genet.* 193: 58–63, 1984) also purified a heat stable protein expressed in *E. coli*, however, they found that the thermal stability of the α-amylase that they were purifying was ligand dependent. The thermal stability in the absence of calcium was approximately 10° C. lower than in the presence of calcium (see FIG. 5, page 61). As a result, these workers added calcium to the medium prior to heating to enhance stability of the enzyme and to recover greater activity. Moreover, this paper also demonstrates that the media conditions can be manipulated in order that the protein of interest is, or becomes, more thermostable than the contaminating *E. coli* proteins. It is of note that these systems require a significant difference between the thermal stability of most of the contaminating proteins and the protein of interest.

Immobilized metal affinity chromatography (IMAC) has also been used in the field of protein purification. For example, recombinant human interleukin-4 has been purified from a crude fermentation broth by passing the broth at pH 7.2 over a zinc charged IMAC column wherein the interleukin-4 is bound, and eluting with 0.5M NaCl or 50 mM EDTA (Tang, J. C. T. et al., U.S. Pat. No. 5,077,388). Interleukin-2 and interferon gamma expressed in mammalian systems have been purified using cation exchange chromatography followed by zinc-charged IMAC (Georgiades, J. A. and Gumulka, J. U.S. Pat. No. 4,723,000). A relatively pure interleukin-2, interferon gamma solution was loaded onto an IMAC column and contaminants were removed from the stream by binding to the column material while the interleukin and interferon flowed through the column. No elution was necessary. Recombinantly produced soluble CD4 receptors have also been purified using IMAC (Staples, Mass. and Pargellis, Calif., U.S. Pat. No. 5,169,936). Contaminants were removed from the partially purified starting solution by eluting with salt and a higher concentration of a weak ligand to the metal charging the IMAC. IMAC has also been used to separate mixtures of relative pure proteins into individual components (Kato, Y. et al., *J. Chrom.* 354: 511–517, 1986). However, immobilized metal affinity chromatography has not been used in the purification of any hemoglobin. Indeed, Figueroa et al., (Figueroa, A. et al., *J. Chromatog.,* 371: 335–352 (1986) noted that hemoglobin was could not be eluted from IMAC columns under mild conditions and did not demonstrate elution of hemoglobin under even relatively strong elution conditions. Moreover, IMAC has not been used to achieve greater than 1000 fold removal of *E. coli* proteins while simultaneously purifying hemoglobin from a lysate to greater than 99% purity.

Soluble rather than immobilized metal affinity chemistry has been used as well. For example, aqueous two-phase metal affinity extraction has been used to purify hemoglobin by complexing a soluble copper-charged, polyethylene glycol charged bidentate chelator with a soluble hemoglobin and complexing the hemoglobin to the soluble chelator to produce a partitioned, two phase system (Wuenschell, G. E., et al., *Bioprocess Eng.* 5: 199–202, 1990).

Carbon monoxide is typically removed from carbonmonoxy hemoglobin solutions by subjecting the solutions to with a strong light under an inert gas or under vacuum (Di Iorio, E. E., *Meth. Enzymol.* 76: 57–72, 1981). Alternatively, carbon monoxide can be removed from carbonmonoxy hemoglobin by heating the solution. However, both light and heat can promote undesired reactions in hemoglobin molecules.

The dissociation equilibrium constant for CO binding has long been known to be much smaller than that for oxygen. Furthermore, it is well known that the chief reason for this is that the rate of dissociation from of carbon monoxide from hemoglobin is much slower that the rate of dissociation of oxygen from hemoglobin. Therefore simply increasing the concentration of oxygen in the hemoglobin solution above does not appear to be a promising technique, because oxygen cannot combine with hemoglobin until the carbon monoxide ligand has first left the molecule, which appeared to be the rate limiting step. Nonetheless, the present invention provides methods for the replacement of carbon monoxide in carbonmonoxy hemoglobin with oxygen by increasing the concentration of oxygen dissolved in the hemoglobin solution.

Metals can also contaminate hemoglobin solutions (Marshall et al. in *Blood Substitutes and Oxygen Carriers*, Chang (ed.), Marcel Dekker, Inc., New York, pp. 267–270, 1993). This kind of contamination may be removed using a number of different methodologies, but the success of a particular method for a particular solution is unpredictable. For example, various chelating resins have been used to separate various metals from a solution, including nickel, although many times such separation is effective only at very low pH and is thus unsuitable for use with hemoglobin solutions (Figura and McDuffie, *Anal. Chem.* 49: 1950–1953, 1977; Darnall et al., *Envir. Sci. Tech.* 20: 206–208, 1986; Vernon, *Chem. and Industry* 15: 634–637, 1977; Moyers and Fritz, *Anal. Chem.* 49: 418–423, 1977; Yip et al., *Anal. Biochem.* 183: 159–171, 1989; Yalpani, M. and Abdel-Malik, M. M., U.S. Pat. No. 4,952,684). Metal chelators, such as ethylenediamine tetraacetate (EDTA) have also been used to remove metal contamination from solution. However, these chelators can be toxic at the concentrations required to remove all metal contamination (Heindorff, K. et al., Mutation Res. 115: 149–173, 1983), and may enhance oxidation of the hemoglobin molecule (Kikugawa, K., et al., *Chem. Pharm. Bull.* 29: 1382–1389, 1981).

Current purification techniques that are suitable for use in the purification of erythrocyte derived hemoglobin, for example anion exchange chromatography, may remove small quantities of *E. coli* derived material, but are not effective for the removal of large quantities of contamination that can be encountered during the purification of hemoglobin solutions containing significant amounts of contaminants, for example, recombinantly produced hemoglobin. Likewise, techniques that have been developed for the purification of recombinantly produced proteins are not applicable to hemoglobin both because of the need to provide extraordinary levels of purification to ensure adequate contaminant removal and the difficulty in economically scaling these processes to produce suitable amounts of hemoglobin. Accordingly, a need exists for general methods of purifying hemoglobin without regard to the source of the hemoglobin material. The present invention satisfies this need and provides related advantages as well.

SUMMARY OF THE INVENTION

The present invention relates to a method for producing a substantially contaminant-free hemoglobin solution comprising obtaining a crude hemoglobin-containing lysate and heating the lysate for a sufficient time and a sufficient temperature to reduce contaminants in the crude hemoglobin-containing lysate to obtain the substantially contaminant-free hemoglobin solution. Contaminants include any soluble contaminants such as microbial proteins, cellular membranes and contaminating hemoglobins such as hemoglobin isoforms, methemoglobin and especially protoporphyrin-IX containing hemoglobin. The crude hemoglobin-containing lysate can be obtained by lysis of any hemoglobin-containing cell whether erythrocyte or non-erythrocyte. In one embodiment, the crude hemoglobin-containing lysate is obtained by lysing bacterial cells that have expressed recombinant hemoglobin. The crude hemoglobin-containing lysate is heated for up to one hour, preferably less than 5 minutes, more preferably less than 1 minute, and even more preferably less than 30 seconds, particularly 10 to 12 seconds. The crude hemoglobin-containing lysate can be heated at temperatures between about 70 to about 90° C., more preferably 75°–85° C., particularly 77°±2° C. or 82°±2° C. Prior to heating, the hemoglobin in the crude hemoglobin-containing lysate can be in a thermally stable state, either deoxygenated or liganded. Preferably the hemoglobin in the hemoglobin-containing lysate is liganded with a liganding gas such as oxygen, carbon monoxide or nitric oxide, preferably carbon monoxide.

In a further aspect of the instant invention, the hemoglobin-containing lysate, whether crude, clarified or substantially contaminant-free is contacted with an immobilized metal affinity chromatography (IMAC) resin charged with a divalent ion, washed with at least one IMAC solution and eluted with an eluting solution to produce a partially purified hemoglobin solution. The divalent metal ion can be copper, cobalt, nickel or zinc and is preferably zinc. In a further aspect of the invention, the IMAC wash solution(s) can comprise salts, buffers and salts, competitive ligands or chelating agents. In one embodiment, the IMAC wash solution comprises competitive ligands such as imidazole and the hemoglobin-containing lysate contains hemoglobin that has been converted to carbonmonoxy hemoglobin.

Still further, the present invention provides for the further purification of a partially purified hemoglobin solution by loading the partially purified hemoglobin solution onto an anion exchange resin, washing the anion exchange resin and eluting the anion exchange resin to obtain a substantially purified hemoglobin solution. The partially purified hemoglobin solution can be exchanged prior to loading onto the anion exchange resin into a suitable solution. Preferably, all solutions for exchanging, washing and eluting of the anion exchange column are cationic. Metals that may have been introduced into the substantially purified hemoglobin solution can be removed by the addition and optional removal of chelating agent such as ethylene diamine tetraacetic acid (EDTA) or diethylamine triamine pentaacetic acid (DTPA, also called pentaacetic acid), more preferably EDTA.

Further, the present invention provides for the removal of carbon monoxide from carbonmonoxy hemoglobin by treating the carbonmonoxy hemoglobin with high concentrations of dissolved oxygen in a hemoglobin solution, preferably achieved by pressurizing a container containing the hemoglobin solution with an oxygen-containing gas, preferably gas containing high percentages of oxygen, more preferably 100% oxygen.

Another aspect of the present invention relates to hemoglobin solutions that are substantially contaminant-free, partially purified, substantially purified, or pure hemoglobin solutions purified according to the methods of the present invention. Pharmaceutical compositions containing such hemoglobin solutions are also provided.

DETAILED DESCRIPTION OF THE INVENTION

Figure 1:
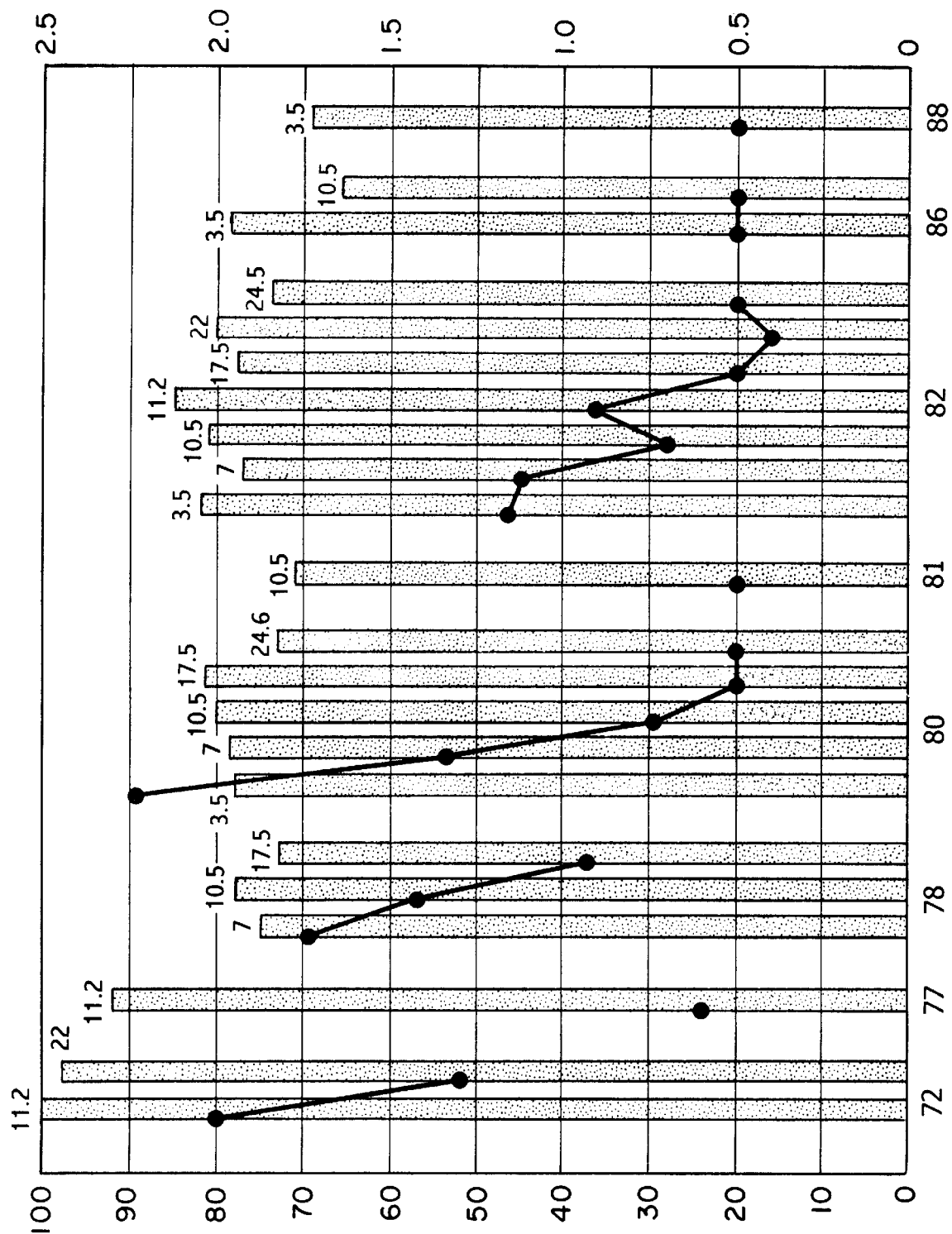
FIG. 1 shows a summary of fully functional hemoglobin yield in percent (gray bars with scale indicated on the left Y-axis) and protoporphyrin IX remaining (● with scale indicated on the right Y-axis) in a protoporphyrin IX-containing hemoglobin solution after heating by steam injection as described in Example 4. Note that 0.4% and 0.5% PIX remaining are at limits of detection. Values are presented for a number of temperatures (X-axis). Heating retention times are noted on the gray bars.

This invention provides processes for the purification of hemoglobin, especially recombinant hemoglobin. In particular, this invention provides methods for the removal of contaminating proteins and hemoglobins by rapidly heating a crude hemoglobin lysate while the hemoglobin is stabilized in the R state or the T state to result in a substantially contaminant-free hemoglobin solution. In a further embodiment, the invention provides for a surprisingly high degree of purification using a single chromatographic step, immobilized metal affinity chromatography (IMAC), to result in a partially purified hemoglobin solutions. The invention further provides for the purification of the partially purified hemoglobin solution using anion exchange chromatography to produce a substantially purified hemoglobin solution, and if needed, the invention provides for removal of metals that may have been introduced during the purification process by addition and then optional removal of a suitable chelating agent to obtain purified hemoglobin. The invention still further provides for methods for removing carbon monoxide from a carbonmonoxy hemoglobin by use of high pressure oxygen treatment. Each of these processes can be used alone, or they can be combined as desired.

Hemoglobin-containing cells suitable as starting material for the present invention are readily available from a number of sources. Such sources include but not limited to outdated human red blood cells, bovine red blood cells and a number of non-red blood cell systems including, but not limited to, bacterial, yeast, plant, and mammalian cells. For example, slaughter houses produce very large quantities of hemoglobin-containing cells. In addition, if a particular species or breed of animal produces a hemoglobin-containing cell especially suitable for a particular use, those creatures may be specifically bred for this purpose in order to supply the needed blood. Also, transgenic animals may be produced that can express a recombinant mutant, non-mutant or transgenic hemoglobin red blood cells and their progenitors. Human blood banks must discard human blood, including hemoglobin-containing cells, after a certain expiration date. Such discarded blood can also serve as a starting material for the present invention.

In addition to expression of hemoglobin in red blood cells and red blood cell progenitors, hemoglobin can be produced in non-erythrocyte cells using recombinant technology. The genes encoding subunits of any desired hemoglobin may be cloned, placed in a suitable expression vector and inserted into microorganism, animal, plant or other organism, or inserted into cultured animal or plant cells or tissues. These organisms, cells or tissues may be produced using standard recombinant DNA techniques and may be grown in cell culture or in fermentations. Human alpha and beta globin genes have been cloned and sequenced by Liebhaber et al. (*Proc. Natl. Acad. Sci. USA* 77: 7054–7058, 1980) and Marotta et al. (*J. Biol. Chem.* 252: 5040–5053, 1977) respectively. Techniques for expression of both native and mutant alpha and beta globins and their assembly into hemoglobin are set forth in U.S. Pat. No. 5,028,588 to S. J. Hoffman, incorporated herein by reference; K. Nagai and Hoffman, S. J. et al., PCT/US90/02654; Townes, T. M. and McCune, S. L., PCT/US91/09624; and De Angelo, J. et al., PCT/US91/02568 and PCT/US91/08108.

The hemoglobin in the hemoglobin-containing starting material that can be purified by the methods of this invention can be either naturally occurring human hemoglobin or any of a variety of hemoglobins from other species, mutant hemoglobins, or hemoglobin-like molecules. Any globin subunit, whether of natural or recombinant origin, of any hemoglobin, can be crosslinked or genetically fused to another globin subunit. Such crosslinking or genetic fusion can occur within a single hemoglobin molecule or between two or more hemoglobin molecules. Particularly preferred hemoglobins are tetrameric hemoglobins, whether or not genetically fused or chemically crosslinked, and multiples of tetrameric hemoglobins (e.g. octamers, dodecamers, etc.), however produced. Therefore, the term hemoglobin encompasses any for example, non-crosslinked hemoglobin, chemically crosslinked hemoglobin, or genetically fused hemoglobin.

In most cases, the first step in the preparation of a pure hemoglobin solution is to get the hemoglobin outside of the hemoglobin-containing cell that has expressed it to produce a crude hemoglobin-containing lysate. This can usually be accomplished by breaking open the cells, e.g., by sonication, homogenization, enzymatic lysis or any other cell breakage technique known in the art. Alternatively, hemoglobin can be released from hemoglobin containing cells by dilution at a controlled rate with a hypotonic buffer so that some contamination with cellular components can be avoided (Shorr et al., U.S. Pat. No. 5,264,555). In addition, cells may be engineered to secrete hemoglobin or any of the hemoglobin subunits. After or concurrent with this first lytic step, a large amount of the various soluble contaminants such as contaminating non-hemoglobin proteins, cell membranes and soluble contaminant hemoglobins, such as protoporphyrin IX-containing hemoglobin, hemoglobin isoforms and methemoglobin, can be removed if needed as prescribed in the present invention by heating the crude hemoglobin-containing lysate, and if necessary, removing precipitated material to produce a substantially contaminant-free hemoglobin solution.

Removal of contaminating cellular components such as non-hemoglobin proteins and cell membranes is important whether or not the source material is red blood cells or bacterial expression systems. The special potentiation of the toxic effects of endotoxin by hemoglobin requires particular attention to the removal of endotoxin contaminants or the prevention of bacterial contamination of the crude starting material (Rausch, C. W. and Feola, M., U.S. Pat. No. 5,084,558). The problem of removal of cellular contamination, particularly bacterial contamination, is especially acute in the setting of expression of recombinant hemoglobin in a bacterial expression system, since, prior to the instant invention, initial high levels of bacterial contamination could not be removed, especially at large commercial scale, without risking the quality of the final product hemoglobin.

In addition to removal of cellular contamination, contaminating hemoglobins such as hemoglobin isoforms, methemoglobin, aggregated hemoglobins, and especially protoporphyrin IX-containing hemoglobins can be removed by heating. Such contaminating hemoglobins can be produced as a result of incorporation of one or more inactive heme groups into a given hemoglobin molecule or a result of oxidation of hemoglobin products during initial production or purification steps. Removal of these contaminating hemoglobins, including protoporphyrin IX-containing hemoglobin, is desirable to maximize product purity and stability.

Heating of the crude hemoglobin-containing lysate can be achieved by any suitable means known to those skilled in the art, which include, but are not limited to, convection/conduction heat exchangers such as tube and shell heat exchangers (e.g. Process Engineers Inc., Hayward, Calif.) and plate and frame heat exchangers (e.g., APV Crepaco Inc., Rosemont, Ill.); steam injection heating, microwave heating (Charm, U.S. Pat. No. 4,975,246) and the like. Most preferably the crude hemoglobin-containing lysate is heated by a means that heats the solutions extremely rapidly. Rapid heating of a solution can occur by, for example, steam injection by combining a steam stream with a stream of crude hemoglobin-containing lysate. Such steam injection can be accomplished using known engineering techniques, such as an in-line static mixer, Venturi mixer or sudden expansion mixer, although the sudden expansion mixer is preferred because of the advantages it affords in avoiding fouling of the fluid stream line. Others are known to those skilled in the art, e.g., *Chemical Engineering Handbook*, 5th edition, McGraw-Hill, N.Y. (1973) pages 6–29 to 6–32. Prior to the introduction of the high heat for the rapid heating, the crude hemoglobin-containing lysate may be prewarmed using suitable heat exchangers known in the art as listed above, most preferably by using a plate and frame heat exchanger (e.g., APV Crepaco Inc., Rosemont, Ill.).

Heating of the crude hemoglobin-containing lysate occurs for a sufficient time and at a sufficient temperature to achieve significant precipitation of contaminating proteins, cell membranes and hemoglobins to yield a substantially contaminant-free hemoglobin solution. Heating can also occur for a sufficient time and at a sufficient temperature so that living microorganisms are killed at the same time contaminant soluble proteins are precipitated. It has now been found that when crude hemoglobin-containing lysates are exposed to heat for a surprisingly short period of time, significant contaminants are removed and adequate inactivation of any intact cells remaining after lysis is achieved.

The crude hemoglobin-containing lysate can be heated up to one hour. More preferably, the hemoglobin lysate is heated for less than 5 minutes, more preferably less than about 1 minute, even more preferably less than 30 seconds, and, under certain conditions, a time of 10 to 12 seconds is preferred.

In order to achieve inactivation and removal of contaminants from crude hemoglobin-containing lysate within these short time periods, it is necessary to heat the crude hemoglobin-containing lysate at a relatively high temperature. Such relatively high temperatures are temperatures above those to which hemoglobin is exposed in its natural environment, i.e., 37° C. Useful temperatures are temperatures greater than about 55° C. and particularly temperatures in the range of about 70° C. to about 90° C., preferably 75°–85° C. It has been found that a temperatures of 77°±2° C. or 82°±2° C. are particularly useful.

FIG. 1 indicates that reduction of contaminants as measured by residual protoporphyrin IX-containing hemoglobin to levels below a preferred one percent level usually occurred only at longer retention times (greater than about 5 seconds) and at higher temperatures (greater than about 70° C). As a result, the most preferred combinations of temperature and time are about 82° C. ±2° C. and between 10 to 25 seconds and 77° C. ±2° C. for between 10 to 25 seconds. However, the selection of the most preferred combination of time and temperature is based on maximizing the amount of precipitation of contaminants, including contaminating hemoglobins, especially protoporphyrin IX-containing hemoglobins, while minimizing loss of the desired hemoglobin.

Significant removal of contaminating proteins and hemoglobins to yield a substantially contaminant-free hemoglobin solution occurs when there is significant removal of contaminating material such as, for example, protoporphyrin-IX containing hemoglobin or *E. coli* proteins (ECP's). For example, ECP's in a substantially contaminant-free hemoglobin solution after heat treatment are reduced 3 to greater than 5 fold compared to the crude hemoglobin-containing lysate. Alternatively, protoporphyrin IX-containing hemoglobins in a substantially contaminant-free hemoglobin solution can be less than about ten percent (10%) of the total hemoglobin, more preferably, less than about six percent (6%) of the total hemoglobin, more preferably less than about one percent (1%) of the total hemoglobin. Most preferably, the protoporphyrin IX-containing hemoglobin in substantially contaminant-free hemoglobin solutions is below the detection limit for protoporphyrin IX in a given measurement technique, for example, as described in Example 5.

During heating, the hemoglobin in the crude hemoglobin-containing lysate can be in either the liganded or unliganded state, but preferably is in either the fully liganded (R-state) or fully unliganded state (T-state) for selective removal of contaminants without substantial loss of the product hemoglobin. R-state hemoglobin ("relaxed") is the high affinity state of hemoglobin and is the dominant form of hemoglobin when a ligand is bound at the heme pocket. Such ligands include oxygen, carbon monoxide and nitric oxide. T-state hemoglobin ("tense") is the low affinity state of hemoglobin and is the dominant form of hemoglobin when it is deoxygenated. T-state hemoglobin is also known as deoxyhemoglobin or simply deoxy.

To ensure that the hemoglobin is either completely in the T-state or completely in the R-state, the crude hemoglobin-containing lysate can be first either deoxygenated (favoring the unliganded or T-state) or the hemoglobin-containing lysate can be treated with a suitable liganding gas (favoring the liganded or R-state).

Deoxygenation can be accomplished by addition of an exogenous chemical reducing agent to the solution, such as dithionite or bisulfite, or by treating the solution with an inert gas such as nitrogen. Deoxygenation can also occur by isolating the crude hemoglobin-containing lysate from contact with the atmosphere and allowing the reducing equivalents in a crude hemoglobin-containing lysate to consume any available oxygen. This latter method is the particularly suitable method of deoxygenation and is particularly suited to crude hemoglobin-containing lysates that are obtained as a result of production of recombinant hemoglobin since the interior cell environment of most suitable host cells, particularly bacterial and yeast cells, is highly reducing. Therefore, a crude hemoglobin-containing lysate derived from the lysis of bacterial or yeast cells, which is essentially a crude solution of reducing cell components, will provide a reducing environment without the need of exogenous chemical reducing agents.

Preferably hemoglobin in a crude hemoglobin containing solution is in the liganded (in the R-state) at the time of heating. Hemoglobin can be liganded with oxygen or non-oxygen ligands by mixing or sparging a crude hemoglobin-containing lysate with a suitable gas mixture. Non-oxygen ligands such as carbon monoxide and nitric oxide are preferred because complete oxygen binding to hemoglobin to produce a fully liganded hemoglobin is difficult to achieve in the reducing environment that is present in the hemoglobin-containing lysate. The mixing of the crude hemoglobin-containing lysate with a liganding gas can occur by sparging and agitating a crude hemoglobin-containing lysate with the liganding gas after the hemoglobin-containing cells have been broken but prior to the heating. Alternatively, the liganding gas can be mixed with the hemoglobin-containing cells prior to harvesting of the cells while the cells are still unbroken or in a fermentor. The preferred non-oxygen gas is carbon monoxide (CO), which can be essentially pure CO or mixtures of CO with other gases such as air, nitrogen, argon, helium or hydrogen (Scott Specialty Gases, Plumsteadville, Pa.). Preferably, the CO is essentially pure CO. The rate of mixing or sparging can be any rate that results in saturation of the hemoglobin in the solution with the liganding gas. For example, the rate of sparging will be a function of the concentration of CO in the sparge gas and can be a specified flow rate of gas (e.g., 0.1–100 standard cubic liters per minute [sclm]) or, alternatively, sparging can continue until a specified amount of the hemoglobin is carbonmonoxy-hemoglobin (also known as carbonylhemoglobin or HbCO). The amount of carbonmonoxy-hemoglobin can be measured using a variety of analytical techniques (Collison et al., *Clin. Chem.* 14: 162, 1968; Johansson and Wollmer, *Clin. Physiol.* 9: 581, 1989; Rodkey et al., *Clin. Chem.* 25: 1388, 1979, Commins and Lawther *Brit. J. Ind. Med.* 22: 139, 1965; Small, *T. Appl. Physiol.* 31(1): 154–160, 1971, Fogh-Andersen et al., *Clin. Chim. Acta* 166: 283–289, 1987; Zwart, A. et al., *Clin. Chem.* 30: 373–79, 1984). A particularly convenient method for the determination of the amount of carbonmonoxy hemoglobin is the spectrophotometric method described by Zwart et al. (supra). This method uses application of a pseudoinverse matrix derived from extinction coefficients of the hemoglobin species of interest.

The methods of the present invention can be used to remove contaminants from a crude hemoglobin-containing lysate to result in a substantially contaminant-free hemoglobin solution substantially free of contaminating cell membranes, precipitated non-hemoglobin proteins and contaminating hemoglobins, particularly protoporphyrin IX-containing hemoglobins. Flocculant aids, such as polyethyleneimine, DEAE cellulose, other poly-cationic flocculants (for example, Magnafloc 573™, Cytec Industries, Indianapolis, Id.) or diatomaceous earth (Eagle-Picher Minerals, Inc.) can be added to aid in the precipitation of cellular debris and contaminating material. In addition, chelating agents, for example ethylene diamine tetraacetic acid (EDTA) or diethylamine triamine pentaacetic acid (DTPA, also called pentaacetic acid), can be added to prevent oxidative damage of the hemoglobin in the solution. Oxidative damage of the hemoglobin in the contaminant-free hemoglobin solution can also be prevented by controlling the oxygen content of the process environment (for example, by blanketing the solid-liquid separation mechanism with an inert gas such as nitrogen). Cellular debris and precipitated contaminants from either a heated or a non-heated crude hemoglobin-containing lysate can be removed by a number of mechanical means suited to solid-liquid separations, including but not limited to sedimentation techniques such as centrifugation and settling; direct capture techniques such as expanded bed or flow through big bead chromatography; and filtration methods, such as vacuum filtration, pressure filtration, tangential flow or cross flow filtration, most preferably rotary drum vacuum filtration. Note that expanded bed or flow through big bead resins can also be immobilized metal affinity chromatography (IMAC) resins that are further discussed below, and thus removal of precipitated contaminating hemoglobins and cellular debris can be combined with IMAC purification in one step. After heating and mechanical removal of cellular debris and precipitated contaminating material, a substantially contaminant-free hemoglobin solution is available for further manipulation. This solution, or indeed, any solution resulting from any of the process steps described herein, can then be used for further applications, such as for example to obtain hemoglobin that can be (1) chemically modified to alter oxygen affinity; (2) used to form tetramers stabilized against dissociation; or (3) used to form polymers. The substantially contaminant-free hemoglobin solutions as described below.

The substantially contaminant-free hemoglobin solution can be treated again with the liganding gas to ensure that all the hemoglobin in the solution is in the appropriate conformation. Additional steps, such as adding chelating agents, controlling the oxygen content of the process environment, or both adding chelating agents and controlling the oxygen content of the process environment can be taken to minimize oxidation of the hemoglobin in the substantially contaminant-free hemoglobin solution. For example, the substantially contaminant-free hemoglobin solution is sparged again with carbon monoxide as described above and EDTA is added to a final concentration of approximately 1 mM.

The substantially contaminant-free hemoglobin solution can then be subjected to immobilized metal affinity chromatography to further remove other hemoglobin and non-hemoglobin contaminants as well as a surprisingly large amount of *E. coli* proteins and other cellular components. Immobilized metal affinity chromatography utilizes metal linked to a bidentate chelator (such as, for example imino-diacetic acid) immobilized on a solid substrate, for example, a resin or a membrane sheet. Suitable IMAC resins include but are not limited to ToyoPearl AF-Chelate 650M (TosoHaas, Inc., Philadelphia, Pa.), Flow Through Big Bead Resin modified for IMAC (Sterogene, Inc., Arcadia, Calif.), Chelating Sepharose Big Bead, Chelating Sepharose 6B™ (both Pharmada, Piscataway, N.J.), most preferably Chelating Sepharose Fast Flow (Pharmada, Piscataway, N.J.). Suitable membrane sheets include but are not limited to Acti-Mode Separation™ (FMC, Inc., Natick, Mass.). As used herein, the term IMAC resin is used to refer to any solid substrate containing an immobilized bidentate chelator such as resins or membrane sheets.

The IMAC resin can be charged with any divalent metal ion, including nickel, copper, cobalt and zinc. Preferably the divalent metal ion used to charge the IMAC resin or sheet is zinc in the form of zinc acetate. Zinc is added to the clarified hemoglobin-containing lysate that is a substantially contaminant-free hemoglobin solution to a final zinc concentration of 2–4 mM using, for example, 1M zinc acetate. After zinc addition, the solution is brought to high pH, preferably greater than 7.0, more preferably pH 8.0 to 8.5 with 0.5 N NaOH. The solution should be maintained between 6 and 20° C. Prior to loading onto the IMAC resin, the solution should be filtered through a filtration device, preferably a depth filter, preferably a CUNO filtration device (Cuno, Inc., Meriden, Conn.) to remove any material that might have been precipitated by the addition of the divalent metal. The IMAC resin should be maintained at a suitable temperature, preferably less than 25° C., more preferably between 4°–15° C., more preferably between 4 and 10° C., and charged with a divalent metal ion as mentioned above. Charging of the resin can be accomplished by passing a solution of the selected metal over the resin in accordance with the manufacturer's recommendations such that all possible metal binding sites are loaded. This charging can occur, for example, by passing at least two column volumes of a 20 mM zinc acetate solution over a Chelating Sepharose Fast Flow column. The charged IMAC resin should then be equilibrated with a salt solution. Preferably, the IMAC resin is equilibrated with at least two column volumes of a salt solution, the salt solution being preferably less than 500 mM NaCl, most preferably 200 mM NaCl. After equilibration, the substantially contaminant-free hemoglobin solution can be loaded onto the charged IMAC resin to a load described by the manufacturer, for example to a load of between 5–100 grams of hemoglobin/liter of resin, most preferably 15–30 g/l.

Contaminating proteins, especially *E. coli* proteins, can be removed from the IMAC resin by washing the resin with sufficient volumes of suitable wash solutions of the same or different pH, buffer/salt solutions of the same or different pH, chelating agents, or suitable competitive ligands. Suitable competitive ligands include histidine, imidazole, Tris, or glycine. Suitable chelating agents include but are not limited to EDTA and DTPA. Suitable wash solutions can include Tris, HEPES, MOPS, triethylamine, triethanolamine, bicarbonate and phosphate. Suitable salts include chloride salts, particularly sodium chloride. If the contaminating bacterially derived proteins are removed by washing with a salt solution, then a particularly useful first wash solution comprises a higher concentration salt solution than the load solution, and preferably the resin is washed with at least two column volumes. In one embodiment, the wash solution is a Tris/NaCl solution, more preferably 20 mM Tris and 0.5M–1M NaCl (preferably 0.5–0.75M NaCl), pH 7.5–9.0 (preferably about pH 8.0–8.5). A second wash can be performed using a second wash solution comprising a buffer and a salt, the buffers including Tris, HEPES, MOPS, triethylamine, triethanolamine, bicarbonate and phosphate, and having lower conductivity than the first wash solution. A useful solution is 10–20 mM Tris, 25–50 mM NaCl, pH 7.5–9.0.

In another embodiment, rather than eluting the material after the first two washes as further described below, removal of contaminating material, particularly *E. coli* proteins, can be enhanced by washing the column with a competitive ligand, particularly imidazole. Sufficient imidazole should be used such that there is adequate removal of *E. coli* proteins, but not sufficient to result in removal of significant amounts of hemoglobin. Suitable concentrations of imidazole are approximately 10 mM±5 mM, pH about 7.0–7.5, preferably pH 7.2. However, the amount of imidazole required to provide adequate removal of contaminants without significant elution of hemoglobin may be higher or lower, and can depend on, for example, the source of the hemoglobin, the load of hemoglobin on the IMAC resin, and the pH of the imidazole wash solution. If imidazole is used to remove large amounts of soluble contaminating proteins from the hemoglobin solution, it must be removed from the column quickly by washing the column with a suitable buffer solution, for example, 20 mM sodium phosphate, 50 mM sodium chloride, pH 6.5. If imidazole is not quickly removed, the hemoglobin bound to the column can suffer oxidative damage. Moreover, the hemoglobin solution should be in the R-state with carbon monoxide bound at the heme groups prior to washing with imidazole so that oxidative damage is reduced to minimal levels.

After removal of contaminating soluble proteins, particularly *E. coli* proteins, by washing of the IMAC resin, the hemoglobin of the present invention can be eluted from the IMAC resin with an eluting solution by increasing the pH or by eluting with a chelating agent or a suitable competitive ligand to produce a partially purified hemoglobin solution. Suitable competitive ligands include histidine, imidazole, Tris, or glycine. Suitable chelating agents include but are not limited to EDTA and DTPA. Most preferably, the hemoglobin of the invention is eluted using a sufficient amount of EDTA in the elution buffer to elute the hemoglobin of the invention, preferably 10–45 mM EDTA at pH 7.5 to 8.5, most preferably 15 mM EDTA at pH 8.0. Elution can occur utilizing any suitable elution scheme, for example by isocratic elution, stepwise elution, stepwise gradient elution or gradient elution. Most preferably elution occurs by isocratic elution. The hemoglobin that is eluted from the column is a partially purified hemoglobin solution. The partially purified hemoglobin solution is a solution that contains 99% by weight hemoglobin relative to other proteins in the solution, and has at least 100 fold less, more preferably 500 fold less, and most preferably 500–1000 fold less *E. coli* proteins than clarified hemoglobin-containing lysate when *E. coli* proteins are measured according to the techniques described in Example 11.

The partially purified hemoglobin solution can then be further purified by anion exchange chromatography. However, prior to anion exchange chromatography, the solution may be brought to the proper pH and ionic conditions for loading onto the desired anion exchange resin. This can be accomplished by dialysis or ultrafiltration against a suitable exchange solution. Most preferably this is accomplished by ultrafiltration against the solution used to equilibrate the anion exchange resin. Suitable components of exchange solutions include alkylamines, aminoethyl alcohol, triethanolamine (TEA), ethylenediamine, Tris and pyridine. Preferably these exchange solutions are solutions of Tris or TEA, more preferably this exchange solution is 20 mM Tris, pH about 8.9 or 25 mM TEA, pH approximately 9. Ultrafiltration can be performed in any suitable ultrafiltration apparatus equipped with a suitable ultrafilter, preferably an ultrafilter of <50,000 nominal molecular weight cutoff (NMCO), more preferably <30,000, most preferably <10,000.

Suitable anion exchange resins are well known in the art, and include but are not limited to Q Sepharose Fast Flow, DEAE Sephadex A-50 (both from Pharmacia, Inc., Piscataway, N.J.), Dowex 1-X8 resin, and AG MP-1 resin (Bio-Rad, Richmond, Calif.). Most preferably Q Sepharose Fast Flow is used to further purify the partially purified hemoglobin solution. After or during the preparation of the partially purified hemoglobin solution for loading onto a Q Sepharose Fast Flow resin, the anion exchange resin itself can be equilibrated by washing with the same exchange solution as was used to prepare the partially purified hemoglobin solution for anion exchange chromatography. As above, this solution can be any suitable solution. Suitable solutions can include alkylamines, aminoethyl alcohol, triethanolamine, ethylenediamine, Tris and pyridine. Preferably these solutions are Tris or triethanolamine, most preferably this solution is 20 mM Tris, pH 8.9 or 25 mM TEA, pH approximately 9. The partially purified hemoglobin solution can be loaded onto the resin to a charge of 5–50 grams of hemoglobin per liter of resin, most preferably 20 grams of hemoglobin per liter of resin. The loaded resin can be washed with any suitable wash solution such as the exchange solution, preferably 15–25 mM Tris, pH 7.5–9.5, more preferably 20 mM Tris, pH 8.9, or 20–30 mM TEA, pH 8.5–9.5, preferably 25 mM TEA, pH approximately 8.9. The loaded resin can be further washed with either the same suitable wash solutions or a different suitable wash solution, such as 10–15 mM Tris, pH 7.5–8.9, more preferably 12 mM Tris, pH 7.7, or 20–25 mM TEA, pH 8.0–8.5, preferably 23 mM TEA, pH approximately 8.2. Elution of the hemoglobin to create a substantially purified hemoglobin-containing solution can be accomplished by lowering the pH to 7.4–7.6, most preferably to pH 7.5, using a suitable buffer as described above, most preferably 12 mM Tris or 13 mM TEA. Elution can occur utilizing any suitable elution strategy, for example, isocratic elution, stepwise elution, stepwise gradient or gradient elution. Most preferably elution occurs by isocratic elution. Conductivity of the elution buffer may be between 550 and 1200 uS/cm, more preferably between 550 and 850 uS/cm, most preferably 700 uS/cm. A substantially purified hemoglobin solution preferably is a hemoglobin solution that meets the following specifications:

| Methemoglobin | <10% (wt/wt) |
| Carbonmonoxyhemoglobin | <5% (wt/wt) |
| E. coli proteins (ECP's) | <50 ppm |
| LAL Endotoxin | <0.5 EU/ml |
| Bioburden | 1 CFU/ml |
| Protoporphyrin IX | <2% (wt/wt heme) |
| EDTA | <5 mg/L |

At this point in the purification, the hemoglobin ligand that was previously added can be removed to produce deoxygenated hemoglobin or can be exchanged with another ligand, preferably oxygen or nitric oxide, most preferably oxygen. This can be accomplished using a number of techniques, including photolysis (Di Iorio, E. E., (1981) in *Methods in Enzymology*, E. Antonini, L Rossi-Bernardi and E. Chiancone, (eds.) Academic Press, NY, pp 57–72); and techniques designed to increase gas mass transfer that are well known in the art (for an example listing of methods see *Chemical Engineering Handbook*, 5th edition, McGraw-Hill, New York (1973) chapter 18). These methods include such techniques as flowing the carbonmonoxyhemoglobin against an oxygen-containing gas stream in a hollow fiber membrane or gas exchange apparatus; diafiltering and sparging the exchanging buffer with oxygen as is diafiltered through an ultrafilter; using a thin-film flow apparatus equipped with a pressurized gas sweep or that allows light mediated carbon monoxide removal; sparging a slow flow trickle-bed with oxygen; or sparging packed beds with oxygen.

A particularly useful technique for removal of carbon monoxide from carbonmonoxy hemoglobin is sparging the solution in a holding tank with oxygen and removing released CO. Preferably the solution is sparged with at least approximately 20% oxygen, more preferably with at least 50% oxygen and even more preferably with 100% oxygen. Preferably the solution is sparged under pressure sufficient to yield dissolved oxygen concentrations of approximately a ten-fold excess of oxygen with respect to hemoglobin, for example, greater than 8 mM preferably greater than 50 psig, more preferably 60–100 psig. If desired, the oxygen can then be removed from the oxyhemoglobin solution by removal of the oxygen by any deoxygenation method in the art to produce a deoxygenated substantially purified hemoglobin solution.

Finally, if contaminating metals have been introduced into the substantially purified hemoglobin solution during the production or processing of the hemoglobin, they can be removed in a further aspect of the invention. This removal can be accomplished by addition of any suitable chelating agent, preferably EDTA or DTPA, most preferably EDTA, to the substantially purified hemoglobin solution and subsequent removal of the added chelating agent if desired, or by diafiltration against a controlled amount of chelating agent, preferably EDTA or DTPA, most preferably EDTA as further described in co-pending application Ser. No. 08/097,273, filed Jul. 23, 1993, to result in a pure hemoglobin solution. A pure hemoglobin solution is preferably a solution that meets the same purity parameters as a substantially purified hemoglobin solution and further contains less than 5 mg/L of nickel. Whether metal removal is necessary or not, the substantially purified hemoglobin solution can be diafiltered into a suitable formulation buffers. Such buffers are described in Hoffman and Nagai, U.S. Pat. No. 5,028,588, Chivers and Belval, U.S. Ser. No. 08/097,273, filed Jul. 23, 1993, Rosenthal and Gerber, U.S. Ser. No. 08/208,740, filed Mar. 8, 1994, and Gerber, Looker and Kerwin, U.S. Ser. No. 08/417,644, filed Apr. 5, 1995, all hereby incorporated by reference. Formulations can further include less than about 25 mM of a chelating agent, preferably EDTA.

For the purposes of the present invention, a pure hemoglobin solution is any hemoglobin solution substantially free of protoporphyrin IX-containing hemoglobin contaminants, endotoxins and contaminating metals, especially nickel, that has the functionality necessary for a given utility. The pure hemoglobin solution can be used as, for example, a source of bio-available iron in dietary supplementation, a highly purified molecular weight marker for laboratory applications, a volume expander and most preferably, as a modifier of the oxygen content of a solution, such as in the case of the use of hemoglobin as an oxygen carrying solution that modifies the oxygen content of blood or the use of hemoglobin to change the oxygen content of a tissue or cell culture.

Pharmaceutical compositions comprising the substantially purified or pure hemoglobin solutions of the invention can be useful for, for example, subcutaneous, intravenous, or intramuscular injection, topical or oral administration, large volume parenteral solutions useful as blood substitutes, etc. Pharmaceutical compositions of the invention can be administered by any conventional means such as by oral or aerosol administration, by transdermal or mucus membrane adsorption, or by injection. Non-pharmaceutical compositions of the invention can be used as, for example, reference standards for analytical instrumentation needing such reference standards, reagent solutions, control of gas content of cell cultures, for example by in vitro delivery of oxygen to a cell culture, and removal of oxygen from solutions.

In one embodiment, the substantially purified hemoglobin solutions or the pure hemoglobin solutions (collectively "purified hemoglobin solutions") obtained by the methods of the instant invention can be formulated for use in therapeutic applications. For example, the purified hemoglobin solutions produced according to the present invention can be used in compositions useful as substitutes for red blood cells in any application that red blood cells are used. Such compositions of the instant invention formulated as red blood cell substitutes can be used for the treatment of hemorrhage where blood volume is lost and both fluid volume and oxygen carrying capacity must be replaced. Moreover, because the compositions of the instant invention can be made pharmaceutically acceptable, the formulations of the instant invention can be used not only as blood substitutes that deliver oxygen but also as simple volume expanders that provide oncotic pressure due to the presence of the large hemoglobin protein molecule. The purified hemoglobin solutions obtained by the methods of the present invention can be used alone in solution or can be part of a suitable pharmaceutical composition such as those described in Hoffman and Nagai, U.S. Pat. No. 5,028,588, Chivers and Belval, U.S. Ser. No. 08/097,273, filed Jul. 23, 1993, Rosenthal and Gerber, U.S. Ser. No. 08/208,740, filed Mar. 8, 1994, and Gerber, Looker and Kerwin, U.S. Ser. No. 08/417,644, filed Apr. 5, 1995.

Doses of hemoglobin as a blood substitute can range from as little as 10 mg to 5 grams or more of extracellular hemoglobin per kilogram of patient body weight, depending on the specific clinical situation (e.g. surgery, trauma, etc.). Thus, a dose for a human patient might be from a few grams to over 350 grams. It will be appreciated that the unit content of active ingredients contained in an individual dose of each dosage form need not in itself constitute an effective amount since the necessary effective amount could be reached by administration of a plurality of administrations as injections, etc. The selection of dosage depends upon the dosage form utilized, the condition being treated, the particular purpose to be achieved according to the determination of the ordinarily skilled artisan in the field.

Administration of extracellular hemoglobin can occur for a period of seconds to hours depending on the purpose of the hemoglobin usage. For example, as a blood delivery vehicle, the usual time course of administration is as rapid as possible. Typical infusion rates for hemoglobin solutions as blood replacements can be from about 100 ml to 3000 ml/hour. However, when used to stimulate hematopoiesis, administration can last only seconds to five minutes and therefore administration rates can be slower because the dosage of hemoglobin is much smaller than dosages that can be required to treat hemorrhage.

In a futher embodiment, the formulation of the instant invention can be used to treat anemia, both by providing additional oxygen carrying capacity in a patient that is suffering from anemia, and by stimulating hematopoiesis. In addition, because the distribution of the hemoglobin in the vasculature is not limited by the size of the red blood cells, the hemoglobin of the present invention can be used to deliver oxygen to areas that red blood cells cannot penetrate. These areas can include any tissue areas that are located downstream of obstructions to red blood cell flow, such as areas downstream of thrombi, sickle cell occlusions, arterial occlusions, angioplasty balloons, surgical instrumentation and the like.

The purified hemoglobin solutions of the instant invention can also be used as replacement for blood that is removed during surgical procedures where the patient's blood is removed and saved for reinfusion at the end of surgery or during recovery (acute normovolemic hemodilution or hemoaugmentation).

Because the purified hemoglobin solutions of the instant invention can bind nitric oxide and other non-oxygen ligands as well as oxygen, the formulations of the instant invention are also useful for the binding or delivery of nitric oxide or non-oxygen ligands. These non-oxygen ligands can be bound or delivered both in vivo or in vitro. For example, the purified hemoglobin solutions of the instant invention may be used to remove excess nitric oxide from a living system. Excess nitric oxide has been implicated in conditions ranging from hypotension to septic shock. Likewise, nitric oxide or other non-oxygen ligands may be delivered to a system to alleviate a disease condition. For example, nitric oxide could be delivered to the vasculature to treat hypertension. Other therapeutic uses of the instant invention can include drug delivery and in vivo imaging.

The purified hemoglobin solutions of the present invention can also be used for a number of in vitro applications. For example, the delivery of oxygen by the purified hemoglobin solutions of the instant invention can be used for the enhancement of cell growth in cell culture by maintaining oxygen levels in vitro. Moreover, the purified hemoglobin solutions of the instant invention can be used to remove oxygen from solutions requiring the removal of oxygen, and as reference standards for analytical assays and instrumentation.

It will be appreciated from the methods and descriptions described herein that the present invention can also be used to remove other contaminants besides bacterial contaminants from hemoglobin solutions, for example, the same process can be used to purify hemoglobin expressed in yeast expression systems.

The foregoing description of the invention is exemplary for purposes of illustration and explanation. It will be apparent to those skilled in the art that changes and modifications will be possible without departing from the spirit and the scope of the invention. It is intended that the following claims be interpreted to embrace all such changes and modifications.

EXAMPLES

The following examples are provided by way of describing specific embodiments of the present invention without intending to limit the scope of the invention in any way.

Example 1

Production of Protein Solution Containing Hemoglobin

A. Construction of a Bacterial System for the Expression of Recombinant Hemoglobin Hemoglobin, denoted rHb1.1, which contained both a glycine bridge between the C terminus of a first alpha globin and the N terminus of a second alpha globin ("di-alpha") and the Presbyterian mutation, was produced by fermentation of one of the strains listed in Table 1, utilizing either plasmid pSGE1.1E4 or pSGE705. The level of expression of rHb1.1 from the two plasmids was approximately the same, independent of the strain used under the same fermentation conditions. Plasmid pSGE1.1E4 is described in Hoffman et al., WO 90/13645. Construction of pSGE705 is described below.

Strain SGE127 carrying the plasmid pSGE1.1E4 is referred to as SGE128. Strain SGE800 carrying pSGE705 is SGE1353. Strain SGE1661 carrying the plasmid pSGE705 is referred to as SGE1662.

TABLE 1

Bacterial Strains

| STRAIN | GENOTYPE |
|---|---|
| SGE127 | F traD36 laci$^q$Δ (lacZ)M15 proBA+ /φ1A$^R$ φ2A$^R$ recA1 thi gyrA96(NalR) endA Δ(lac-proBA) hsdR17 relA1 supE44 |
| SGE800 | gyrA96(Nal$^R$) endA hsdR17 relA1 supE44, φ1A$^R$, φ2A$^R$, φ3A$^R$ recJ |
| SGE1661 | gyrA96(Nal$^R$) endA hsdR17 relA1 supE44, φ1A$^R$, φ2A$^R$, φ3A$^R$, φ4A$^R$, recJ |

φ1A, φ2A, φ3A, and φ4A are phage isolated from the fermentation area. φ1A appears to be T5. φ2A, φ3A, and φ4A have not yet been identified but are not T phage.

Materials. pBR322, pUC19 and pNEB193 were purchased from New England Biolabs (Beverly, Mass.). Most plasmids used for the preparation of pSGE705 are described in Table 2. Oligonucleotides were synthesized on an Applied Biosystems DNA Synthesizer Model 392 (Foster City, Calif.). The oligonucleotides used in preparing pSGE705 are listed in Table 3. Restriction endonucleases were purchased from New England Biolabs (Beverly, Mass.) and used according to manufacturer's specifications. T4 DNA ligase was purchased from either New England Biolabs (Beverly, Mass.) or Gibco-BRL (Gaithersburg, Md.) and used according to manufacturer's specifications. Pfu polymerase was purchased from Stratagene (La Jolla, Calif.) and used according to manufacturer's specifications.

Media used are described in J. H. Miller, *Experiments in Molecular Genetics*. (Cold Spring Harbor Press, Cold Spring Harbor, N.Y., 1972) and J. H. Miller, *A Short Course in Bacterial Genetics* (Cold Spring Harbor Press, Cold Spring Harbor, N.Y., 1992). Acridine orange, ampicillin and kanamycin sulfate were purchased from Sigma Chemical Co. (St. Louis, Mo.). Tetracycline was purchased from Aldrich Chemicals (Milwaukee, Wis.).

Genetic and Molecular Biological Procedures. Standard bacterial genetic procedures are described in J. H. Miller, *Experiments in Molecular Genetics*. (Cold Spring Harbor Press, Cold Spring Harbor, N.Y., 1972) and J. H. Miller, *A Short Course in Bacterial Genetics* (Cold Spring Harbor Press, Cold Spring Harbor, N.Y., 1992). Standard molecular biology procedures were performed as described by Sambrook (Sambrook et al., *Molecular Cloning*, Cold Spring Harbor Press, Cold Spring Harbor, N.Y., 1989.

Plasmid DNA Transformation. DNA transformations were performed by the procedure described by Wensick (Wensick et al., *Cell* 3: 315–325, 1974). Briefly, cells were grown to mid log phase and then pelleted, resuspended in an equal volume of 10 mM MgSO$_4$ and incubated on ice for 30 minutes. The cells were centrifuged and the pellet resuspended in ½ original volume of 50 mM CaCl$_2$ and placed on ice for 20 minutes. The cells were centrifuged again and then resuspended in 1/10 original volume of 50 mM CaCl$_2$. Plasmid DNA was added to the competent cells in a solution of 10 mM Tris-HCl pH 8.0, 10 mM MgCl$_2$ and 10 mM CaCl$_2$. The mixture was incubated on ice for 15 minutes and then incubated at 37° C. for 5 minutes. One milliliter of LB medium was added and the mixture incubated with shaking for 30–60 minutes. The culture was then centrifuged, resuspended in 0.1 ml of LB medium and plated on the appropriate selective medium. SGE1662 was prepared by a one-step transformation method (Chung, C. T., et al., *Proc. Natl. Acad. Sci.* 86: 2172–2175, 1989) which introduced pSGE705 into SGE1661.

Purification of DNA. DNA fragments were purified from an agarose gel using the Geneclean system (Bio 101, Inc. La Jolla, Calif.; method provided with product). PCR products were prepared and cleaved with restriction endonucleases using the Double Geneclean system (Bio 101, Inc. La Jolla, Calif.; method provided with product). Briefly, the PCR product was purified away from the PCR primers, then the PCR product was cleaved with restriction endonuclease(s) and purified from the restriction endonuclease and buffer. The PCR product was then ready for ligation reactions.

TABLE 2

Plasmids

| PLASMID | DESCRIPTION |
|---|---|
| pSGE1.1E4 | rHb1.1 expression plasmid containing di-alpha and beta genes |
| pSGE1.1E5 | pSGE1.1E4 but ampicillin resistant instead of tetracycline resistant |
| pSGE490 | pUC19 lacI on a Bam HI-Hind III fragment |
| pSGE491 | pUC19 α on an Eco RI-Xba I fragment |
| pSGE492 | pNEB193 Ptac-α |
| pSGE493 | pUC19 β on an Xba I-Hind III fragment |
| pSGE500 | pUC19 α β on a Bam HI-Hind III fragment |
| pSGE504 | pSELECT-1 replace Sty I with a Pme I site |
| pSGE505 | pSGE504 rrnB T1 transcriptional terminator in the Eco RI-Cla I sites |
| pSGE507 | ColE1 ori and tet, 2213 bp |
| pSGE509 | ColE1 ori tet lacI, 3425 bp |
| pSGE513 | ColE1 ori tet lacI α β, 4386 bp |
| pSGE515 | ColE1 ori tet lacI diα β, 4812 bp |
| pSGE700 | pTZ18U + diα β from pSGE515 |
| pSGE705 | modified rHb1.1 expression plasmid, ColE1 ori, tet, lacI, diα and β genes |
| pTZ18U | a phagemid derivative of pUC19, for oligonucleotide directed mutagenesis |
| pDLII-91F | pGEM1 + α missing valine in 2nd position (Des-val) |
| pNEB193 | pUC19 with more restriction sites in the multi cloning sites |
| pBR322 | ColE1 ori tet amp |
| pRG1 | pACYC177 lacI$^q$ |

TABLE 3

Oligonucleotides

| OLIGO | SEQUENCE (5'–3') | DESCRIPTION |
|---|---|---|
| EV18 SEQ. ID #1 | CGGGAATACGGTCTAGATCATTAACGGTATTTCGAAGTCAGAACG | C-term of α gene, Xba I site |
| EV27 SEQ. ID #2 | GATCCGAGCTGTTGACAATTAATCATCGGCTCGTATAATGTGTGGA ATTGTGACGGATAACAATTTCACACAGGAAATTAATTAATGCT GTCTCC | tac promoter sequence, Bam HI-Eag I sites |
| EV28 SEQ. ID #3 | GGCCGGAGACAGCATTAATTAATTTCCTGTGTGAAATTGTTATC CGCTCACAATTCCACACATTATACGAGCCGATGATTAATTGTCA ACAGCTCG | tac promoter sequence, Bam HI-Eag I sites, complement of EV27 |
| EV29 SEQ. ID #4 | TCGGATTCGAATTCCAAGCTGTTGGATCCTTAGATTGAAC TGTCTCCGGCCGATAAAACCACCG | 5' end of α with Eco RI, Bam HI and Eag I sites |
| EV30 SEQ. ID #5 | CGGAAGCCCAATCTAGAGGAAATAATATATGCACCTGACTCCG GAAGAAAAATCC | 5' end of β with Xba I site |
| EV31 SEQ. ID #6 | CCCGAAACCAAGCTTCATTAGTGAGCTAGCGCGTTAGCAACACC | 3' end of β with Hind III site |
| MW007 SEQ. ID #7 | TTTAAGCTTCATTAGTGGTATTTGTGAGCTAGCGCGT | mutagenesis reverse primer, adds last 3 codons of β for pSGE515 |
| MW008 SEQ. ID #8 | CAGCATTAATTAACCTCCTTAGTGAAATTGTTATCCG | mutagenesis reverse primer to optimize α ribozyme binding site (RBS) |
| MW009 SEQ. ID #9 | GGTGCATATATTTACCTCCTTATCTAGATCATTAACGGTATTTCG | mutagenesis reverse primer to optimize β RBS and remove second Bgl II site |
| TG14 SEQ. ID #10 | GGTTTAAACC | Pme I linker |
| TG59 SEQ. ID #11 | GGCGAATAAAAGCTTGCGGCCGCGTTGACACCATCGAATG GCGCAAAACCTTTCGCGG | Upstream of lacI gene, has a Hind III and a Not I site upstream of the promoter |
| TG60 SEQ. ID #12 | GGGCAAATAGGATCCAAAAAAAAGCCCGCTCATTAGG CGGGCTTTATCACTGCCCGCTTTCCAGTCGGG | Downstream side of lacI gene with the trp transcriptional terminator and a Bam HI site |
| TG62 SEQ. ID #13 | CCCCGAAAAGGATCCAAGTAGCCGGCGGCCGCGTTCCACTG AGCGTCAGACCCC | upstream primer for pBR322 ori positions 3170–3148 with a Bam HI and a Not I site |
| TG63 SEQ. ID #14 | GGCGGTCCTGTTTAAACGCTGCGCTCGGTCGTTCGGCTGCGG | downstream primer for pBR322 ori positions 2380–2404 with Pme I site |

Annealing of oligonucleotides. Complementary oligonudeotides were annealed according to the following procedure. Equimolar amounts of each oligonucleotide were mixed in 15–25 μl of 10 mM Tris-HCl pH 8.0/1 mM EDTA and incubated at 65° C. for 30 minutes. The sample was transferred to a 37° C. water bath for 30 minutes. Finally, the sample was incubated on ice for 60 minutes or overnight in the refrigerator.

Oligonudeotide directed mutagenesis. Oligonudeotide directed mutagenesis was performed with the Muta-gene phagemid in vitro mutagenesis kit (Bio-Rad, Hercules, Calif.) according to manufacturer's instructions which are based on the method of Kunkel (Kunkel, T. A., *Proc. Natl. Acad. Sci. USA* 82: 488, 1985; Kunkel et al., *Methods Enzymol.* 154: 367, 1987). The rHb1.1 region of pSGE515 was cloned into pTZ18U (Bio-Rad, Hercules, Calif. or U.S. Biochemical, Cleveland, Ohio) on a Bam HI-Hind III fragment to create pSGE700. Three oligonucleotides, MW007, MW008 and MW009 were used to simultaneously introduce multiple changes in a single reaction.

Preparation of pBR322 ori. PCR primers were designed to amplify the pBR322 origin of replication. These primers, TG62 and TG63, annealed to the positions 2380–2404 and 3170–3148 on the pBR322 DNA sequence (Sutcliffe, J. G., *Cold Spring Harbor Symp. Ouant. Biol.* 43: 77–90, 1979). The PCR product was digested with Not I and Pme I. The DNA fragment was purified according to the Geneclean procedure.

Preparation of tet gene fragment. The source for the tet gene was pSELECT-1 (Promega Corp., Madison, Wis.). This plasmid has a number of restriction endonuclease sites, such as Bam HI, Hind III, Sal I and Sph I removed from the tet gene (Lewis and Thompson, *Nucleic Acids Res.* 18: 3439–3443, 1993). A Pme I linker was inserted into the Sty I site of pSELECT-1. This plasmid was designated pSGE504. Oligonucleotides TG71 and TG72 were annealed and ligated to the Eco RI-Cla I fragment of pSGE504. This plasmid, pSGE505, was shown to have the expected restriction endonuclease sites and to have lost the sites present in the multicloning site of pSELECT-1. pSGE505 was digested with Not I and Pme I. The 1417 bp fragment was purified according to the Geneclean protocol.

Preparation of lacI gene. The lacI gene was isolated by amplifying the gene sequence from pRG1 (a gift from R.

Garcia, Dana-Farber Cancer Inst., Boston, Mass.) that carried the lacI gene. The PCR primers, TG59 and TG60, were designed to generate a wild type lacI promoter (Farabaugh, P. J., *Nature* 274: 765, 1978) upstream of the gene and to place the trp terminator sequence (Christie et al., *Proc. Natl. Acad. Sci. USA* 78: 4180–4184, 1981) downstream of the gene. The same step could be carried out using Y1089 (Promega) or chromosomal DNA from any *E. coli* strain carrying the lac region, such as MM294 (ATCC 33625.) The PCR product was gel purified and isolated according to the Geneclean procedure and cloned into Bam HI-Hind III digested pUC19 DNA to make pSGE490.

Construction of pSGE515. PCR primers EV29 and EV18 were chosen to amplify the alpha gene from pDLII-91F (Hoffman et al., WO 90/13645). The purified PCR product was cleaved with the restriction endonucleases Eag I and Xba I.

To create a plasmid that contained $P_{tac}$-α, the alpha gene (from above) and the tac promoter, which was prepared by annealing EV27 and EV28, were mixed with Eco RI-Xba I cleaved pUC19 DNA. The mixture of the three DNA fragments, in approximately equimolar ratio, was treated with T4 DNA ligase. After incubation the ligation mixture was used to transform SGE476 (equivalent to MM294, ATCC 33625) and ampicillin resistant transformants were selected. (Transformation into Strain MM294 (ATCC 33625) would yield equivalent results.) An isolate with the correct restriction endonuclease fragments (consistent with FIG. 2) was designated pSGE492. The α gene and the tac promoter DNA sequences were verified by DNA sequencing.

Primers EV30 and EV31 were used to amplify the β gene from pSGE1.1E4 by PCR. The purified β gene fragment was digested with Xba I and Hind III and then mixed with Xba I -Hind III digested pUC19 DNA and treated with T4 DNA ligase. The ligation mixture was used to transform competent SGE476 and transformants were selected on LB+ampicillin (100 μg/ml) plates. An isolate that contained the appropriate restriction endonuclease fragments (consistent with FIG. 2) was chosen and designated pSGE493. The β gene was confirmed by DNA sequencing.

The β gene was isolated from pSGE493 by restriction with Xba I and HindIII followed by purification according to the Geneclean method. This DNA fragment was then ligated to Xba I-Hind III restricted pSGE492 DNA and transformed into SGE713. (Any dam strain such as JM110 (ATCC 47013) or GM119 (ATCC 53339) could also be used.) An ampicillin resistant transformant that carried a plasmid that had the appropriate restriction fragments (consistent with FIG. 2) was chosen and designated pUC19αβ (pSGE500).

The Bam HI-Hind III fragment that contained the α and β genes of pSGE500 was purified according to the Geneclean method. An Xho I fragment that carried a portion of the di-α gene containing the glycine linker region was gel purified from pSGE1.1E5. pSGE1.1E5 (described in Hoffman et al., U.S. Ser. No. 789,179, filed Nov. 8, 1991) is a tetracydine sensitive analogue of pSGE1.1E4 (Hoffman et al., WO 90/13645), which could also have been used.

The pBR322 origin of replication region (pBR322 ori, above) was ligated to the tet gene fragment (above) and the ligation mixture was transformed into SGE476. (Transformation into MM294, above would yield equivalent results.) Tetracycline resistant transformants were selected and plasmid DNA was isolated and analyzed. An isolate that contained the appropriate restriction endonuclease fragments (consistent with FIG. 2) was chosen and designated pSGE507.

Next, pSGE507 and pSGE490 were digested with Bam HI and Not I and the appropriate fragments (consistent with FIG. 2) were purified. The two purified fragments were ligated together and the ligation mixture was used to transform competent SGE713. (Any dam strain could also be used; see above.) Tetracycline resistant transformants were selected, and plasmid DNA was isolated and analyzed. A plasmid that had the appropriate restriction fragments (consistent with FIG. 2) was chosen and designated pSGE509.

The purified Bam HI-Hind III fragment of pSGE500 that contained the α and β genes was ligated to Bam HI-Hind III digested pSGE509. The ligation mixture was used to transform pSGE713 (see above for equivalent strains) and tetracycline resistant transformants were selected and characterized. An isolate yielding the correct size plasmid with the expected restriction endonuclease fragments (consistent with FIG. 2) was chosen and designated pSGE513.

The Xho I fragment of pSGE1.1E5 (described in Hoffman et al., U.S. Ser. No. 789,179, filed Nov. 8, 1991) that contained the di-α glycine linker sequence was ligated to Xho I digested pSGE513 to create a plasmid that contained the di-α gene. SGE753 was transformed with the ligation mixture and tetracycline resistant transformants were selected. (Transformation into SGE800 would have yielded equivalent results.) Isolates were screened to identify those that contained the Xho I fragment inserted into pSGE513 in the correct orientation (consistent with FIG. 2). An isolate that contained the correct configuration of the di-α gene, as determined by restriction endonuclease analysis with Eag I, was designated pSGE515.

Modification of pSGE515 to create pSGE705. The DNA sequence record used to design PCR primers for the amplification of the β gene did not contain the C-terminal three amino acids. Oligonucleotide directed mutagenesis was used to add these nine nucleotides to the DNA sequence of the β gene. In the same reactions, modifications were introduced to optimize the ribosome binding sites for the di-α and β genes, and to remove a Bgl II site near the end of the di-α gene.

In the construction of the plasmid, one of the last steps was the modification of the ribosome binding sites to optimize the sequences. The following are the changes that were made with the oligonucleotides MW008 and MW009.

```
di alpha
before  -  CAATTTCAC - - AGGAAATTAATTAATGCTG       SEQ. ID #15
           | | | | | | | | | * * | | | | * * | | | | | | | | | | | | |
alpha   -  CAATTTCACTAAGGAGGTTAATTAATGCTG          SEQ. ID #16
```

Four nucleotide changes, shown above, including the insertion of two nucleotides, were introduced with MW008 to optimize the ribosome binding site for di-alpha (| -indicates identity, *-indicates a change).

beta before - TAAaGATCTAGA- - -GGAAATAA-TATATGCAC    SEQ. ID #17
         | | | * | | | | | | | * * * | | | * * | | | * | | | | | | | | |
after  - TAATGATCTAGATAAGGAGGTAAATATATGCAC      SEQ. ID #18

The six nucleotide changes shown above, including the insertion of four nucleotides, were introduced with MW009 to optimize the ribosome binding site for beta. The lower case "a" on the before strand was a T to A mutation in the construction of the alpha gene that introduced a Bgl II site into the sequence. This was removed so that there would only be a single Bgl II site in pSGE705 (|)-indicates identity, *-indicates a change).

End of Beta before - CTCGCTCAC- - - - - - - - -TAATGAA    SEQ. ID #19
         | | | | | | | | | * * * * * * * * * | | | | | | |
after  - CTCGCTCACAAATACCACTAATGAA            SEQ. ID #20

MW007 introduced the coding sequence for the last three amino acids of the beta gene as shown above (|-indicates identity, *-indicates a change).

Putative mutants were screened for loss of a Bgl II restriction endonuclease cleavage site (introduced by MW008). Seventeen of 24 had lost the site and were further characterized by DNA sequencing at the other two mutagenized sites. One of the 17 had incorporated all three modifications. These changes were verified by DNA sequencing and the rHb1.1 genes were cloned into Bam HI-Hind III digested pSGE509. An isolate that had the correct restriction endonuclease fragments was designated pSGE705.

Figure 2:
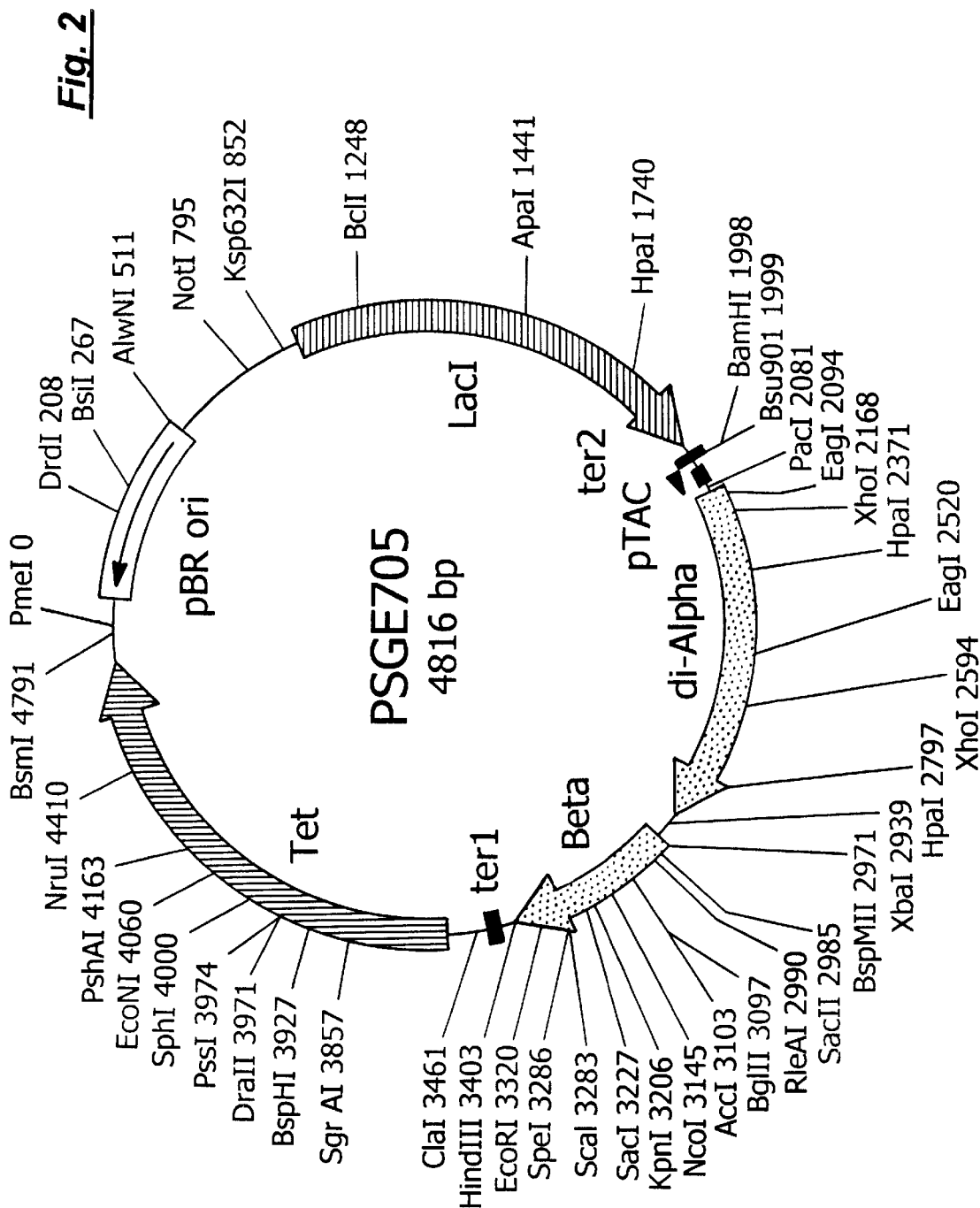
FIG. 2 shows a plasmid map of pSGE705, a plasmid used in the recombinant expression of a mutant hemoglobin, rHb1.1. The plasmid map includes relevant restriction sites.

A plasmid map of pSGE705 is shown in FIG. 2. The plasmid map indicates many of the restriction endonuclease cleavage sites. pSGE705 is smaller than its counterpart, pSGE1.1E4, and the placement of its restriction sites facilitates modular alterations of the sequence. An unused antibiotic resistance marker was removed, and a promoter was added to the lacI gene that would allow tighter control of rHb1.1 expression.

A new sequence upstream of the α gene minimized the distance between the tac promoter (De Boer et al., Proc. Natl. Acad. Sci. 80: 21–25, 1983) and the first codon of the alpha gene. The intergenic region between the di-α gene and the β gene was also designed to contain the minimum sequence that contained a restriction endonuclease site and the ribosome binding site for the β gene.

On Nov. 10, 1993 E. coli strains SGE127 and SGE800 were deposited with the American Type Culture Collection, 12301 Parklawn Drive, Rockville, Md. (ATCC Accession Numbers 69485 and 69484, respectively); E. coli strain SGE1661 was deposited Jan. 20, 1994 (ATCC Accession Number 55545). Deposits were made under the terms of the Budapest Treaty on the International Recognition of the Deposit of Microorganisms for the Purposes of Patent Procedure and the Regulations thereunder (Budapest Treaty). This assures maintenance of a viable culture for 30 years from the date of deposit. The organisms will be made available by the ATCC under the terms of the Budapest Treaty, and subject to an agreement between Applicants and ATCC which assures unrestricted availability upon issuance of the pertinent U.S. patent. Availability of deposited strains is not to be construed as a license to practice the invention in contravention of the rights granted under the authority of any government in accordance with its patent laws.

B. Fermentations

The six hundred liter fermentation procedures described below were used to obtain material for purification and functionality determinations.

Seed Stock

Seed stock was grown up in LB broth containing 10 g/L BactoTryptone™, 5 g/L yeast extract, 5 g/L NaCl, 0.2 g/L NaOH, and 10 ug/ml tetracycline to an optical density of 1.5–1.7 at 600 nm. The solution was then made up to 10% glycerol and stored at −80° C. until required.

Fermentor Inoculum (500 ml broth in 2 L shake flasks)

To prepare the fermentor inoculum, seed stock was thawed and 0.1–0.4 ml of seed stock were inoculated into 500 ml of a solution containing approximately 4 g/L $KH_2PO_4$,7 g/L $K_2HPO_4$,2 g/L $(NH_4)_2SO_4$,1 g/L $Na_3$ Citrate.$2H_2O$,153 mg/L $MgSO_4.7H_2O$,2.3 g/L of L-proline,2 g/L yeast extract, 4.8–5 g/L glucose, 75 mg/L thiamine HCl, 12 mg/L tetracycline, 81 mg/L $FeCl_3.6H_2O$, 4 mg/L $ZnCl_2$,6 mg/L $CoCl_2.6H_2O$, 6 mg/L $Na_2MoO_4.2H_2O$,3.1 mg/L $CaCl_2.2H_2O$, 3.9 mg/L $Cu(II)SO_4.5H_2O$, 1.5 mg/L $H_3BO_3$, and 300 μl/L HCl. This culture was allowed to grow for 10 hours at 37° C. on a shaker. Four flasks were combined and used to inoculate the Seed Fermentors.

Seed Fermentor (14 L volume in 20 L Fermentor)

The entire fermentor inoculum was then aseptically transferred to a 20-liter fermentor containing 10 liters the following: 1.8 g/L $KH_2PO_4$,3.3 g/L $K_2HPO_4$,1.8 g/L $(NH_4)_2SO_4$,155 mg/L thiamine HCl,10.3 mg/L tetracycline,3.1 g/L proline,1.9 g/L $MgSO_4.7H_2O$,1.9 g/L $Na_3$-citrate.$2H_2O$,133 mg/L $FeCl_3.6H_2O$,6.4 mg/L $ZnCl_2$,9.9 mg/L $CoCl_2.6H_2O$, 9.9 mg/L $Na_2MoO_4.2H_2O$,5 mg/L $CaCl_2.2H_2O$,6.3 mg/L $Cu(II)SO_4.5H_2O$,2.5 mg/L $H_3BO_3$,and 494 μl/L HCl. Note that masses of added reagents are calculated using the final volume of fermentation, 14 liters and are approximate within measurement error. The pH was maintained at 6.8 to 6.95 by addition of 15% to 30% $NH_4OH$, dissolved oxygen was maintained at or above 20%, and 50 to 70% glucose was added throughout the growth period, sufficient to maintain low but adequate levels of glucose in the culture (0.1 g/L–10 g/L). Dissolved oxygen was maintained as close to 20% as possible. The culture was grown between 28° and 32° C. for approximately 12 hours prior to transfer to the 600 liter fermentor.

Production Fermentor

The entire seed fermentor inoculum was then aseptically transferred to a 600-liter fermentor containing approximately 375 liters of the solution containing: 1.8 g/L $KH_2PO_4$,3.3 g/L $K_2HPO_4$,1.8 g/L $(NH_4)_2SO_4$,3.3 ml/L polypropylene glycol-2000, 220 g/L glucose,143 mg/L thiamine HCl,9.4 mg/L tetracycline 1.4 g/L $MgSO_4.7H_2O$,1.4 g/L $Na_3$-citrate.$2H_2O$,2.9 g/L L-proline,99 mg/L $FeCl_3.6H_2O$,4.8 mg/L $ZnCl_2$,7.3 mg/L $CoCl_2.6H_2O$,7.3 mg/L $Na_2MoO_4.2H_2O$,3.7 mg/L $CaCl_2.2H_2O$, 4.7 mg/L $Cu(II)SO_4.5H_2O$,1.8 mg/L $H_3BO_3$, and 366 μl/L HCl. Note the reagent additions are calculated with the final volume of the fermentation, 450 liters and that all masses are approximate.

The pH was maintained at 6.8–6.95 by addition of 15% to 30% $NH_4OH$, dissolved oxygen was maintained at or above 20%, and 50–70% glucose was added throughout the growth period, sufficient to maintain low but adequate levels of glucose in the culture (0.1 g/L–10 g/L). The culture was grown between 25° and 30° C. to an $OD_{600}$~10–40 prior to induction with 10–1000 μM IPTG. Upon induction of hemoglobin synthesis, the *E. coli* heme biosynthesis was supplemented by addition of hemin dissolved in 1N NaOH, either by addition of the total mass of hemin required at induction, by continuous addition of hemin throughout the induction period, or by periodic addition of hemin dissolved in 50 mM to 1M NaOH (e.g. one third of the total mass of hemin to be added to the fermentor was added at induction, another third was added after ¼ of the total time after fermentation had elapsed, and the last third was added half-way through the induction period). Total hemin added ranged from 50 to 300 mg/L. The fermentor was allowed to continue for 8–12 hours post-induction. At the end of this period, several 1 ml aliquots were removed from the broth for determination of hemoglobin production and protoporphyrin IX content.

Although most of the material used for purification was produced by fermentation at the 600 liter scale, some was prepared in the 1000 liter scale. Fermentations at this scale differed little from 600 liter scale fermentations, except in the areas discussed below.

Fermentor inocula were grown in 2.5 liter final volumes rather than 0.5 liter final volumes. However, they were grown in the same medium as described for the 500 ml inoculum. Seed fermentations were performed using a 110 liter final volume rather than a 14 liter final volume, and the fermentations were performed using a slightly different medium containing 2.6 g/L $KH_2PO_4$, 4.6 g/L $K_2HPO_4$, and 2.6 g/L $(NH_4)_2SO_4$. All other components were as described for the 14 liter seed fermentor. Production fermentations were performed exactly as described for the 450 liter fermentations, except that the final volume of the fermentation was 1100 liters.

Example 2

Heating of Crude Deoxy Hemoglobin-Containing Lysates with a Tube and Shell Heat Exchanger Fermentations were performed as described in Example 1 with *E. coli* strains SGE127 or SGE800 which contained the plasmids pSGE1.1E4 and pSGE705 respectively. The two strains produced the same mutant hemoglobin and the fermentation products were essentially the same. Unwashed *E. coli* cells (100–300 L) were broken with a Niro homogenizer. The crude lysates were heated with a tube and shell design heat exchanger for 1.6–36 seconds at 70°–90° C. 5 ml of 50% MAGNAFLOC 573 (Cytec Industries, Indianapolis, Id.) solution/L of lysate, was then added and the lysate was clarified by centrifugation.

Protoporphyrin IX and heme could not be accurately quantitated in any lysate material, whether crude or clarified due to interference from other species (hemin and other fermentation products and components). Thus for protoporphyrin IX determinations, samples were prepared using immobilized metal affinity chromatography charged with zinc. Material that had been prepared using IMAC was suitable for protoporphyrin IX determination and reflected the same proportion of protoporphyrin IX that was present in the lysate (demonstrated by spike recovery experiments).

Immobilized metal affinity chromatography was performed using a chelating Sepharose Fast Flow 6B (Pharmacia, Inc., Piscataway, N.J.) column charged with 2 column volumes of 20 mM $Zn(OAc)_2$. The column was then equilibrated with 2 column volumes of 200 mM NaCl. Clarified *E. coli* lysate prepared from unwashed cells was brought up to 1–2 mM $Zn(OAc)_2$, filtered, and then loaded onto the column. The column was washed with 4 column volumes of 500 mM NaCl/20 mM Tris, pH 8.3–8.5, and then further washed with 4 column volumes of 20 mM Tris, pH 8.3–8.5. Captured hemoglobin was eluted from the column with 15 mM EDTA, pH 8.5. The column was then cleaned with 2 column volumes of 200 mM NaCl followed by 2 column volumes of 0.5N NaOH.

Example 3

Effect of Temperature on the Efficiency of Protoporphyrin IX Removal with Rapid Heating under Deoxy Conditions The cells from two fermentations with two different strains of *E. coli*, SGE127 and SGE800 containing the plasmids pSGE1.1E4 and pSGE705, respectively, were broken with the Niro homogenizer (40° C.). No specific process steps were taken to ensure either deoxygenated or liganded conditions, but spectral analysis of the crude lysate solutions demonstrated that all the hemoglobin in the solutions was in the deoxygenated state. The crude *E. coli* lysate contained sufficient reducing power to maintain the solution in the deoxygenated state. Four portions of the crude solution were heated using a tube and shell heating apparatus (Process Engineers Inc., Hayward, Calif.) for 6 seconds at 70, 80, 85, and 90° C.

Example 4

Heating of a Crude Hemoglobin-Containing Lysate-Liganded Conditions

Hemoglobin produced by fermentations as in Example 1 with both *E. coli* strains SGE127 and SGE800 containing the plasmids pSGE1.1E4 and pSGE705, respectively, was sparged with 99.99% carbon monoxide at a flow rate of about 5 standard cubic liters per minute or alternatively, hemoglobin was produced by fermentations as in Example 1 with *E. coli* strain SGE1661 containing the plasmid pSGE705, and sparged with 99.99% carbon monoxide at a flow rate of about 300–500 mls/min so that there was a calculated stoichiometric excess of carbon monoxide relative to all available ligand binding sites in the solution. All sets of fermentations produced comparable results.

After sparging, the crude hemoglobin-containing lysate was preheated in a plate and frame apparatus (APV Crepaco Inc., Rosemont, Ill.) to a temperature of 55° C. then heated for a length of time at a specific temperature by steam injection of the preheated crude hemoglobin-containing lysate. Steam injection heating results in nearly instantaneous heating of the liquid. A variety of heating temperatures and retention times were examined.

All combinations of time and temperature and ligand choice described in Examples 2–4 resulted in substantially contaminant-free hemoglobin solutions with significantly reduced protoporphyrin IX-containing hemoglobin concentrations, as demonstrated in FIG. 1. The final amount of contaminant hemoglobins as determined by monitoring protoporphyrin IX-containing hemoglobin in the lysate after heating decreased slowly from 40–80° C., and rapidly between 80–90° C. (FIG. 1). These data demonstrated that *E. coli* lysates heated between 80–90° C. had the most significant decreases in protoporphyrin IX-containing hemoglobin. However, heating the lysate above 85–90° C. resulted in a loss of rHb1.1 (FIG. 1). These data demonstrated that the removal of protoporphyrin IX-containing hemoglobin was increased at higher temperatures or longer retention times. However, the data also showed that removal of hemoglobin was also increased at higher temperatures and longer retention times, irrespective of the conditions under which the heating took place.

Example 5

Method of Measuring Protoporphyrin IX Content

The determinations of the protoporphyrin IX (PIX) content in hemoglobin samples were accomplished by HPLC (high pressure liquid chromatography) analysis based on the separation of heme and protoporphyrin IX from globin on a reversed phase column. Samples were diluted to approximately 1 mg/ml hemoglobin prior to analysis. To ensure that all heme compounds were quantitated with the same color factor, all heme in the solution was oxidized to hemin before analysis. This was accomplished by mixing $K_3[Fe(CN)_6]$ with the hemoglobin sample just before injection of the sample onto the column to oxidize $Fe^{2+}$ in heme to $Fe^{3+}$. Elution of heme, protoporphyrin IX, and globins was accomplished by an increasingly nonpolar buffer gradient (e.g., water/TFA to acetonitrile). Spectra of hemin and protoporphyrin IX are similar, with absorption maxima at 398 nm and 405 nm, respectively. At 396 nm, color factors for heme and protoporphyrin IX were almost equal, therefore the areas under each peak correspond directly to the relative content of each component. Levels of protoporphyrin IX less than approximately 0.4% (protoporphyrin IX/heme+protoporphyrin IX) were considered to lie below the detection limit of the analytical methodology. Spectral measurements are made anywhere in the range of about 390–410 nm with similar results.

Example 6

Method of Producing a Substantially Contaminant-free Hemoglobin Solution

Hemoglobin was produced as described in Example 1. The fermentor contents were then cooled to 10° C. and adjusted to approximately pH 8.0. After adjustment, the fermentor broth (containing the unbroken *E. coli* cells) was then directly fed to a Niro homogenizer set at a break pressure of 800 bar, with an inlet pressure of 17 psi at a flow rate of 5.7–6.3 liters/min. After one passage through the homogenizer, the stream of cellular debris and hemoglobin was sparged with 100% carbon monoxide at 400 cc/min and directed through a plate and frame pre-heater and warmed to 55° C. The effluent from the pre-heater was then directed to a sudden expansion mixer where contaminating hemoglobins such as protoporphyrin IX-containing hemoglobin and hemoglobin isoforms as well as other bacterial contaminants and hemoglobin isoforms were removed by heating by steam injection to 82° C.±2° C. for approximately 11 seconds. Similar results were obtained by heating for approximately 30 seconds at approximately 77° C. or, alternatively, 30 seconds or less at 72° C. The crude cell lysate was then cooled to 25° C. before further processing. After chilling, diatomaceous earth was added to the solution to a final concentration of 12% (wt/wt) and loaded onto a rotary drum vacuum filter that had been pre-coated with diatomaceous earth. Filtration of the lysate resulted in a substantially contaminant-free hemoglobin solution that was resparged inline with carbon monoxide prior to collection. Protoporphyrin IX content of the crude cell lysate was measured after cell breakage and prior to any processing as described in Examples 2 and 6, and then again after RDVF filtration using the same techniques. Results are shown in FIG. 1 and demonstrate that a substantially contaminant-free, particularly protoporphyrin IX-free hemoglobin solution was produced at temperatures of 72° C. or higher for retention times of approximately 11 seconds or more.

Example 7

Method of Producing a Partially Purified Hemoglobin Solution

The substantially contaminant-free hemoglobin solution was produced as described in Example 6 and was then further processed as described below. The solution was maintained between 6–20° C. during all processing steps unless otherwise stated. One molar zinc acetate was added to the substantially contaminant-free hemoglobin solution to yield a final zinc concentration in the solution of 2 mM, and the pH was adjusted between 8.35–8.5. Because the addition of zinc and the change in pH resulted in precipitation of zinc-complexed material, the solution was re-clarified by depth filtration through a CUNO filtration device equipped with Zeta Plus 90LA filters (Cuno, Inc., Meriden, Conn.). The solution was then further processed using a chelating Sepharose Fast Flow 6B (Pharmacia, Inc., Piscataway, N.J.) column charged with 2 column volumes of 20 mM Zn(OAc)$_2$. The column was then equilibrated with 2 column volumes of 200 mM NaCl. The substantially contaminant-free hemoglobin solution was then loaded onto the column at a load of approximately 20 grams hemoglobin/liter of resin. The column was washed with 4 column volumes of 20 mM Tris/750 mM NaCl, pH 8.35–8.5, and then further washed with 4 column volumes of 10 mM Tris/25 mM NaCl, pH 8.35–8.5. Captured hemoglobin was eluted from the column with 6–8 column volumes of 15 mM EDTA, pH 8.5. The column was then cleaned with 2 column volumes of 200 mM NaCl followed by 3 column volumes of 0.5N NaOH. Linear flow rates for all steps were between 100–200 cm/hr; the column was maintained at 4°–10° C. The partially purified hemoglobin solution was then characterized by protein analysis to determine the degree of purification across the IMAC separation step. Hemoglobin in the contaminant-free hemoglobin solution was quantitated by centrifugation, filtration through a 0.2 μm filter, immobilized metal (zinc) affinity chromatography as described in Example 2 for protoporphyrin IX determinations and detection at 412 nm. Hemoglobin in the partially purified hemoglobin solution was determined by absorbance at 540 nm. Total protein in the starting material (substantially contaminant-free solution) was determined by a Bradford assay using bovine serum albumin as a standard (Bradford, M., *Anal. Biochem.* 72: 248, 1976). Total protein in the partially purified hemoglobin solution produced after immobilized metal affinity chromatography could not be determined because any remaining protein that was not hemoglobin was below the detection limits of the Bradford assay, thus a specific assay for *E. coli* proteins was used (see Example 11 for details). Three runs were compared for purification across the IMAC purification step with the following results:

TABLE 4

| | Hemoglobin Purity | | | | |
|---|---|---|---|---|---|
| Protoporphyrin IX-free Hemoglobin Solution | | | Partially Purified Hemoglobin Solution | | |
| rHb1.1 (g/l) | Total Protein (g/L) | Purity (%) (rHb1.1/total protein) | rHb1.1 (g/L) | *E. coli* proteins (g/L) | Purity (%) (rHb1.1/total protein) |
| 0.99 ± 0.15 | 2.73 ± 0.90 | 38.12 ± 8.8 | 9.70 ± 0.7 | .00747 ± .0054 | 99.92 ± 0.05 |

Example 8

Further Removal of *E. coli* Proteins using Imidazole Washes

The substantially contaminant-free hemoglobin solution was produced as described in Example 6 and was then further processed as described below to yield a partially purified hemoglobin solution. The pH of the substantially contaminant-free hemoglobin was adjusted to pH8.0, containing 1 mM EDTA and 4 mM $Zn(OAc)_2$ was loaded onto an equilibrated 20 cm bed height IMAC resin (Pharmacia Chelating Sepharose FastFlow column) charged with zinc. Next, the loaded column was 20 washed with 2 column volumes of 20 mM Tris, 500 mM NaCl, pH 8.0, 2 column volumes of 20 mM Tris, 50 mM NaCl, pH 8.0, 10 column volumes of 10 mM imidazole, pH 7.2 and finally 4 column volumes of 20 mM sodium phosphate, 50 mM NaCl, pH 6.5. The column eluate was fractionated, and fractions were analyzed by ELISA as described in Example 11. *E. coli* protein removal using the additional imidazole wash was compared to ECP removal when no imidazole wash was utilized (Table 5). It was noted that the use of the imidazole wash resulted in effective, robust and reproducible removal of ECP's irrespective of the level of ECP's in the substantially contaminant-free hemoglobin.

TABLE 5 ng ECP/mg rHb1.1 for partially purified, substantially purified and pure hemoglobin solutions produced with and without imidazole washes in the IMAC step.

| Run # | Partially purified Hemoglobin | | Substantially Purified Hemoglobin | | Pure Hemoglobin Solution | |
|---|---|---|---|---|---|---|
| | No Imidazole | Imidazole | No Imidazole | Imidazole | No Imidazole | Imidazole |
| 1 | 2.2 | 0.53 | ~0.55 | <0.37 | <0.16 | <0.16 |
| 2 | >52 | 0.60 | 16 | <0.20 | >11 | <0.16 |
| 3 | 1700 | 3.8 | 170 | <0.41 | 45 | <0.16 |

Example 9

Method of Producing A Substantially Purified Hemoglobin Solution

A partially purified hemoglobin solution was produced as described in Examples 7 and 8. After IMAC separation, the partially purified hemoglobin solution was then ultrafiltered in a tangential flow filter fitted with 10,000 NMCO filters (Millipore, Inc., Bedford, Mass.). Ultrafiltration both concentrated the partially purified hemoglobin solution and allowed exchange of the buffer to 20 mM Tris, pH 8.9, which was the buffer required for loading onto the anion exchange resin. During the preparation of the partially purified hemoglobin solution for loading onto a Q Sepharose Fast Flow column (an anion exchange column), the column itself was equilibrated by washing with the same buffer as was used to prepare the partially purified hemoglobin solution, 20 mM Tris, pH 8.9. The partially purified hemoglobin solution was then loaded onto the column to a charge of 20 grams of hemoglobin per liter of resin. The loaded column was washed with 12 mM Tris, pH 7.7, conductivity of 700 uS/cm, and finally eluted by lowering the pH to pH 7.5,12 mM Tris. The solution was then oxygenated by sparging the solution under pressure with oxygen while the solution was recirculated until HbCO was less than 3%.

Example 10

Method of Producing A Pure Hemoglobin Solution

Contaminating metals, particularly nickel, were removed from the substantially purified hemoglobin solution produced using the methods of Examples 7, 8 and 9 by the following procedure. One millimolar EDTA was added to the oxygenation tank and the solution was allowed to incubate for 30 minutes prior to ultrafiltration. The oxygenated, EDTA treated hemoglobin solution was transferred to the Millipore ultrafiltration system described above and concentrated 5–6 fold. Diafiltration then began into formulation buffer (150 mM NaCl, 5 mM sodium phosphate, pH 7.4) and was continued until EDTA was less than approximately 5 ppm to produce a pure hemoglobin solution.

Ten batches of pure hemoglobin were prepared according to Examples 7, 8, 9 and 10 above and were characterized using the techniques described in Examples 6 and 11. The solutions had, on average, the following characteristics:

| | |
|---|---|
| $P_{50}$ | 30.32 torr |
| Hill max ($n_{max}$) | 2.3 |
| Methemoglobin | 3.6% |
| Carbonmonoxyhemoglobin | 3.5% |
| *E. coli* proteins (ECP's) | <4 ppm * |
| LAL Endotoxin | <0.03 EU/ml |
| Bioburden | 0 CFU/ml |
| Protoporphyrin IX | <0.4%** |
| Nickel | 29 ug/L |
| EDTA | <5 mg/L* |

*Limit of quantitation of the assay
**0.4% protoporphyrin IX was the limit of quantitation of the assay; 60% of the values were below this limit, the maximum protoporphyrin IX content obtained for the remaining 40% of the values was 0.58%.

Example 11

Purity and Functionality Determinations

Purity and functionality of the hemoglobin solutions were measured as follows: nickel was measured in the final solution by atomic adsorption spectroscopy as described by B. Welz in *Atomic Absorption Spectroscopy* (1985, Verlagsgesellschaft, Weinheim, Germany); $P_{50}$ and Hill coefficients were determined at 37° C. as described in U.S. Pat. No. 5,028,588; and protoporphyrin IX-containing hemoglobin was measured as described in Example 6.

EDTA levels were determined chromatographically by taking a sample of purified hemoglobin and diluting the purified hemoglobin to a concentration of 10 mg/ml with formulation buffer (150 mM NaCl, 5 mM sodium phosphate, pH 7.4) prior to analysis. 100 ul of a 10 mg/ml $FeCl_3.6H_2O$ solution was then added to 900 ul of the diluted sample. The iron-treated material was then ultrafiltered through a 30,000 NMCO filter (Centricon, Arnicon, Boston, Mass.) and the permeate was analyzed on an ODS-Hypersil™ reverse phase chromatography column (5 μm; 100×2.1 mm) (Hewlett Packard, Palo Alto, Calif.). Separations were achieved by isocratic elution with a buffer composed of 910 ml water, 160 ml methanol, 10 ml of 55% (wt/vol) tetrabutyl ammonium hydroxide, pH 6.0. The column was then cleaned with a buffer composed of 400 ml water, 600 ml methanol, 10 ml tetrabutyl ammonium hydroxide, pH 6.0. EDTA elution was monitored at 254 nm and the peaks assigned to EDTA were quantitated against an EDTA standard.

Endotoxin was determined using the chromogenic LAL assay produced by Cape Cod and Associates (Falmouth, Mass.) according to the manufacturer's directions.

ECP's were measured using an ELISA double sandwich format immunoassay. The coating antibody for ECP quantitation of imidazole wash versus non-imidazole wash material (Example 8) was directed against the population of ECP's derived from *E. coli* strain SGE 1661 (described herein) that would co-eluted with hemoglobin from the anion exchange column. The coating antibody for all other ECP measurements was a commercially available antibody directed against a crude lysate of *E. coli* strain K-12 (Dakopatts, Inc., Glostrup, Denmark). For all assays, the detecting antibody was the same as the coating antibody conjugated to horseradish peroxidase. The enzyme substrate was TMB (3,3',5,5'tetramethylbenzidine). For assays using the K-12 derived antibody, the ECP standard was generated by purification of an *E. coli* lysate through two cation exchange columns and represented the ECP's removed by the final anion exchange step of the process. For assays using antibodies to material derived from SGE 1661, the ECP standard was the material that would have co-eluted with hemoglobin as described above.

The foregoing description of the invention is exemplary for purposes of illustration and explanation. It will be apparent to those skilled in the art that changes and modifications will be possible without departing from the spirit and the scope of the invention. It is intended that the following claims be interpreted to embrace all such changes and modifications.

What is claimed is:

1. A method for producing a partially purified hemoglobin solution comprising:
   (a) contacting a hemoglobin-containing lysate with an immobilized metal affinity chromatography (IMAC) resin charged with a divalent metal ion;
   (b) washing the IMAC resin with at least one IMAC wash solution; and
   (c) eluting the IMAC resin with an eluting solution to obtain the partially purified hemoglobin solution.

2. The method of claim 1, wherein the divalent metal ion is nickel, copper, cobalt or zinc.

3. The method of claim 2, wherein the divalent metal ion is zinc.

4. The method of claim 1, wherein the hemoglobin-containing lysate is a clarified hemoglobin-containing lysate.

5. The method of claim 4, wherein the clarified hemoglobin-containing lysate is a substantially protoporphyrin IX-free hemoglobin solution.

6. The method of claim 1, wherein washing the IMAC resin with at least one IMAC wash solution in step (b) comprises:
   washing the IMAC resin with a first IMAC wash solution; and
   washing the IMAC resin with a second IMAC wash solution, wherein the first IMAC wash solution is the same or different than the second IMAC wash solution.

7. The method of claim 6, wherein the first and second IMAC wash solutions comprise Tris, a salt, and a pH greater than 7.

8. The method of claim 6, wherein the first IMAC wash solution comprises about 20 mM Tris, about 0.5 to about 0.75M NaCl, and a pH greater than or equal to 7.5 and wherein the second IMAC wash solution comprises about 5 to about 19 mM Tris, about 0.25 to about 0.75M NaCl, and a pH greater than or equal to 7.6.

9. The method of claim 8, wherein the second IMAC wash solution has a lower conductivity than the first IMAC wash solution.

10. The method of claim 6 further comprising:
washing the IMAC resin with a third IMAC wash solution containing a competitive ligand; and
washing the IMAC resin with a fourth IMAC wash solution to remove said competitive ligand.

11. The method of claim 10, wherein the competitive ligand is imidazole.

12. The method of claim 1, wherein the hemoglobin-containing lysate is treated with a liganding gas prior to step (a).

13. The method of claim 12, wherein the liganding gas is selected from the group consisting of oxygen, carbon monoxide and nitric oxide.

14. The method of claim 13, wherein the liganding gas is carbon monoxide.

15. The method of claim 1, wherein the IMAC resin is eluted by a change in pH, a chelating agent or a competitive ligand.

16. The method of claim 15, wherein the IMAC resin is eluted by a chelating agent.

17. The method of claim 16, wherein the chelating agent is ethylenediamine tetraacetic acid in an eluting solution having a pH no less than about 7.

18. The method of claim 15, wherein said competitive ligand is imidazole.

19. The method of claim 1, wherein the hemoglobin-containing lysate contains recombinant hemoglobin.

20. The method of claim 1, wherein the hemoglobin-containing lysate is obtained by lysis of microbial cells.

21. The method of claim 20, wherein the microbial cells are bacterial cells.

22. The method of claim 21, wherein the bacterial cells are *E. coli*.

23. The method of claim 6, wherein:
said hemoglobin-containing lysate is converted to a substantially contaminant-free recombinant hemoglobin solution prior to contact with the IMAC resin;
said divalent metal ion is zinc;
said first IMAC wash solution contains about 500 to 750 mM NaCl, about 20 mM Tris, pH of about 8.0 to about 8.3;
said second IMAC wash solution contains about 25 mM to 50 mM NaCl, about 20 mM Tris, pH of about 8.0 to about 8.3; and
said IMAC resin is eluted with about 15 mM ethylenediamine tetraacetic acid at a pH of about 8.0.

24. The method of claim 11, wherein:
said hemoglobin-containing lysate is converted to a substantially contaminant-free recombinant hemoglobin solution prior to contact with the IMAC resin;
said divalent metal ion is zinc;
said first IMAC wash solution contains about 500 to 750 mM NaCl, about 20 mM Tris, pH of about 8.0 to about 8.3;
said second IMAC wash solution contains about 25 mM to 50 mM NaCl, about 20 mM Tris, pH of about 8.0 to about 8.3;
said third IMAC wash solution contains about 5 to 15 mM imidazole, pH about 7.2;
said fourth IMAC wash solution contains about 20 mM sodium phosphate, about 50 mM NaCl, pH of about 6.5;
said substantially contaminant-free recombinant hemoglobin solution is liganded with carbon monoxide; and
said IMAC resin is eluted with about 15 mM ethylenediamine tetraacetic acid at a pH of about 8.5.

25. A partially purified hemoglobin solution produced according to the method of claim 1.

26. The method of claim 1, further comprising:
(d) loading the partially purified hemoglobin solution onto an anion exchange resin;
(e) washing the anion exchange resin; and
(f) eluting the anion exchange resin with a second eluting solution to obtain a substantially purified hemoglobin solution.

27. The method of claim 26, further comprising exchanging the partially purified hemoglobin solution into an exchange solution prior to loading onto said anion exchange resin.

28. The method of claim 27, wherein washing the anion exchange resin comprises:
washing the anion exchange resin with the exchange solution; and
washing the anion exchange resin with an anion exchange wash solution having a lower pH than the exchange buffer.

29. The method of claim 28, wherein the second eluting solution has a lower pH than the anion exchange wash solution.

30. The method of claim 29, wherein the exchange solution, anion exchange wash solution and the second eluting solution are cationic.

31. The method of claim 30, wherein:
the exchange solution comprises about 10 to about 30 mM Tris with a pH of about 8.5 to about 9.5;
the anion exchange wash solution comprises about 10 to about 15 mM Tris with a pH of about 7.6 to about 7.9; and
the second eluting solution comprises about 10 to about 15 mM Tris with a pH of about 7.4 to less than about 7.6.

32. The method of claim 31, wherein the exchange solution is about 20 mM Tris with a pH of about 8.5, the anion exchange wash solution is about 12 mM Tris with a pH of about 7.7, and the second eluting solution is about 12 mM Tris with a pH of about 7.5

33. The method of claim 30, wherein:
the exchange solution comprises about 10 to about 30 mM TEA with a pH of about 8.5 to about 9.5;
the anion exchange wash solution comprises about 20 to about 30 mM TEA with a pH of about 7.5 to about 8.5; and
the second eluting solution comprises about 10 to about 30 mM TEA with a pH of about 7.0 to less than about 8.0.

34. The method of claim 26, wherein the exchange solution is about 25 mM TEA with a pH of about 8.9, the anion exchange wash solution is about 23 mM TEA with a pH of about 8.2, and the second eluting solution is about 13 mM TEA with a pH of about 7.5

35. The method of claim 26, wherein the hemoglobin-containing lysate is treated with a liganding gas prior to step (a).

36. The method of claim 35, further comprising removing said liganding gas by exposing said substantially purified hemoglobin solution to oxygen and simultaneously removing carbon monoxide gas.

37. The method of claim 36, wherein said exposure is under high pressure.

38. The method of claim 37, wherein the high pressure is between 60 and 100 psig.

39. The method of claim 36, further comprising: (g) adding a chelating agent to obtain said substantially purified hemoglobin solution.

40. The method of claim 39, further comprising: (h) removing said chelating agent to obtain a purified hemoglobin solution.

41. The method of claim 39, wherein said chelating agent is ethylenediamine tetraacetic acid.

42. A substantially purified hemoglobin solution produced by a method comprising:
(a) contacting a hemoglobin-containing lysate with an immobilized metal affinity chromatography (IMAC) resin charged with a divalent metal ion;
(b) washing the IMAC resin;
(c) eluting the IMAC resin to obtain the partially purified hemoglobin solution;
(d) loading the partially purified hemoglobin solution onto an anion exchange resin;
(e) washing the anion exchange resin; and
(f) eluting the anion exchange resin to obtain the substantially purified hemoglobin solution.

43. The substantially purified hemoglobin solution of claim 42 formulated in a pharmaceutically acceptable formulation buffer.

44. A method for producing a substantially purified hemoglobin solution, comprising:
(a) obtaining a crude hemoglobin-containing lysate;
(b) heating said crude hemoglobin-containing lysate for a sufficient time and at a sufficient temperature to reduce contaminants in said crude hemoglobin-containing lysate to obtain the substantially contaminant-free hemoglobin solution;
(c) contacting the substantially contaminant-free hemoglobin solution with an immobilized metal affinity chromatography (IMAC) resin charged with a divalent metal ion;
(d) washing the IMAC resin;
(e) eluting the IMAC resin to obtain the partially purified hemoglobin solution;
(f) loading the partially purified hemoglobin solution onto an anion exchange resin;
(g) washing the anion exchange resin; and
(h) eluting the anion exchange resin to obtain the substantially purified hemoglobin solution.

45. The method of claim 44, further comprising: (i) removing carbon monoxide by exposure of the substantially purified hemoglobin solution to oxygen.

46. The method of claim 45, further comprising: (j) adding a chelating agent to the substantially purified hemoglobin solution.

47. The method of claim 46, further comprising: (k) removing said chelating agent to obtain the pure hemoglobin solution.

48. The method of claim 44, wherein said contaminants are protoporphyrin IX- containing hemoglobin.

49. A substantially purified hemoglobin solution produced by the method of claim 44.

50. The substantially purified hemoglobin solution of claim 49 formulated in a pharmaceutically acceptable formulation buffer.

51. A purified hemoglobin solution produced by the method of claim 47.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
    ( A ) LENGTH: 45
    ( B ) TYPE: nucleic acid
    ( C ) STRANDEDNESS: single
    ( D ) TOPOLOGY: linear ( i i ) MOLECULE TYPE: C-term of a gene, Xba I site ( i i i ) HYPOTHETICAL: no ( x i ) SEQUENCE DESCRIPTION: SEQ ID NO:1:

CGGGAATACG GTCTAGATCA TTAACGGTAT TTCGAAGTCA GAACG                45

( 2 ) INFORMATION FOR SEQ ID NO:2:

( i ) SEQUENCE CHARACTERISTICS:
    ( A ) LENGTH: 95
    ( B ) TYPE: nucleic acid
    ( C ) STRANDEDNESS: single
    ( D ) TOPOLOGY: linear ( i i ) MOLECULE TYPE: tac promoter sequence, Bam HI-Eag I sites ( i i i ) HYPOTHETICAL: no ( x i ) SEQUENCE DESCRIPTION: SEQ ID NO:2:

GATCCGAGCT GTTGACAATT AATCATCGGC TCGTATAATG TGTGGAATTG            50

TGACGGATAA CAATTTCACA CAGGAATTA ATTAATGCTG TCTCC                  95

( 2 ) INFORMATION FOR SEQ ID NO:3:

( i ) SEQUENCE CHARACTERISTICS:
    ( A ) LENGTH: 96
    ( B ) TYPE: nucleic acid
    ( C ) STRANDEDNESS: single
    ( D ) TOPOLOGY: linear ( i i ) MOLECULE TYPE: tac promoter, Bam HI - Eag I sites ( i i i ) HYPOTHETICAL: no ( x i ) SEQUENCE DESCRIPTION: SEQ ID NO:3:

GGCCGGAGAC AGCATTAATT AATTTCCTGT GTGAAATTGT TATCCGCTCA            50

CAATTCCACA CATTATACGA GCCGATGATT AATTGTCAAC AGCTCG                96

( 2 ) INFORMATION FOR SEQ ID NO:4:

( i ) SEQUENCE CHARACTERISTICS:
 ( A ) LENGTH: 64
 ( B ) TYPE: nucleic acid
 ( C ) STRANDEDNESS: single
 ( D ) TOPOLOGY: linear ( i i ) MOLECULE TYPE: 5'end of alpha gene,with EcoR1, BamH1 and Eag1 sites ( i i i ) HYPOTHETICAL: no ( x i ) SEQUENCE DESCRIPTION: SEQ ID NO:4:
TCGGATTCGA ATTCCAAGCT GTTGGATCCT TAGATTGAAC TGTCTCCGGC CGATAAAACC ACCG ( 2 ) INFORMATION FOR SEQ ID NO:5:

( i ) SEQUENCE CHARACTERISTICS:
 ( A ) LENGTH: 55
 ( B ) TYPE: nucleic acid
 ( C ) STRANDEDNESS: single
 ( D ) TOPOLOGY: linear ( i i ) MOLECULE TYPE: 5'end of beta with Xba I site ( i i i ) HYPOTHETICAL: no ( x i ) SEQUENCE DESCRIPTION: SEQ ID NO:5:

CGGAAGCCCA ATCTAGAGGA AATAATATAT GCACCTGACT CCGGAAGAAA   50

AATCC   55

( 2 ) INFORMATION FOR SEQ ID NO:6:

( i ) SEQUENCE CHARACTERISTICS:
 ( A ) LENGTH: 44
 ( B ) TYPE: nucleic acid
 ( C ) STRANDEDNESS: single
 ( D ) TOPOLOGY: linear ( i i ) MOLECULE TYPE: 3'end of the beta gene with Hind III site ( i i i ) HYPOTHETICAL: no ( x i ) SEQUENCE DESCRIPTION: SEQ ID NO:6:

CCCGAAACCA AGCTTCATTA GTGAGCTAGC GCGTTAGCAA CACC   44

( 2 ) INFORMATION FOR SEQ ID NO:7:

( i ) SEQUENCE CHARACTERISTICS:
 ( A ) LENGTH: 37
 ( B ) TYPE: nucleic acid
 ( C ) STRANDEDNESS: single
 ( D ) TOPOLOGY: linear ( i i ) MOLECULE TYPE: mutagenesis reverse primer ( i i i ) HYPOTHETICAL: no ( x i ) SEQUENCE DESCRIPTION: SEQ ID NO:7:

TTTAAGCTTC ATTAGTGGTA TTTGTGAGCT AGCGCGT   37

( 2 ) INFORMATION FOR SEQ ID NO:8:

( i ) SEQUENCE CHARACTERISTICS:
 ( A ) LENGTH: 37
 ( B ) TYPE: nucleic acid
 ( C ) STRANDEDNESS: single
 ( D ) TOPOLOGY: linear ( i i ) MOLECULE TYPE: mutagenesis reverse primer ( i i i ) HYPOTHETICAL: no ( x i ) SEQUENCE DESCRIPTION: SEQ ID NO:8:

CAGCATTAAT TAACCTCCTT AGTGAAATTG TTATCCG  37

( 2 ) INFORMATION FOR SEQ ID NO:9:

( i ) SEQUENCE CHARACTERISTICS:
    ( A ) LENGTH: 45
    ( B ) TYPE: nucleic acid
    ( C ) STRANDEDNESS: single
    ( D ) TOPOLOGY: linear ( i i ) MOLECULE TYPE: mutagenesis reverse primer ( i i i ) HYPOTHETICAL: no ( x i ) SEQUENCE DESCRIPTION: SEQ ID NO:9:

GGTGCATATA TTTACCTCCT TATCTAGATC ATTAACGGTA TTTCG  45

( 2 ) INFORMATION FOR SEQ ID NO:10:

( i ) SEQUENCE CHARACTERISTICS:
    ( A ) LENGTH: 10
    ( B ) TYPE: nucleic acid
    ( C ) STRANDEDNESS: single
    ( D ) TOPOLOGY: linear ( i i ) MOLECULE TYPE: Pme I linker ( i i i ) HYPOTHETICAL: no ( x i ) SEQUENCE DESCRIPTION: SEQ ID NO:10:

GGTTTAAACC  10

( 2 ) INFORMATION FOR SEQ ID NO:11:

( i ) SEQUENCE CHARACTERISTICS:
    ( A ) LENGTH: 58
    ( B ) TYPE: nucleic acid
    ( C ) STRANDEDNESS: single
    ( D ) TOPOLOGY: linear ( i i ) MOLECULE TYPE: oligonucleotide upstream of lacI gene ( i i i ) HYPOTHETICAL: no ( x i ) SEQUENCE DESCRIPTION: SEQ ID NO:11:

GGCGAATAAA AGCTTGCGGC CGCGTTGACA CCATCGAATG GCGCAAAACC  50

TTTCGCGG  58

( 2 ) INFORMATION FOR SEQ ID NO:12:

( i ) SEQUENCE CHARACTERISTICS:
    ( A ) LENGTH: 69
    ( B ) TYPE: nucleic acid
    ( C ) STRANDEDNESS: single
    ( D ) TOPOLOGY: linear ( i i ) MOLECULE TYPE: downstream side of lacI gene ( i i i ) HYPOTHETICAL: no ( x i ) SEQUENCE DESCRIPTION: SEQ ID NO:12:

GGGCAAATAG GATCCAAAAA AAAGCCCGCT CATTAGGCGG GCTTTATCAC  50

TGCCCGCTTT CCAGTCGGG  69

( 2 ) INFORMATION FOR SEQ ID NO:13:

( i ) SEQUENCE CHARACTERISTICS:
    ( A ) LENGTH: 54
    ( B ) TYPE: nucleic acid
    ( C ) STRANDEDNESS: single
    ( D ) TOPOLOGY: linear ( i i ) MOLECULE TYPE: primer for pBR322 ori positions 3170-3148

( i i i ) HYPOTHETICAL: no ( x i ) SEQUENCE DESCRIPTION: SEQ ID NO:13:

CCCCGAAAAG GATCCAAGTA GCCGGCGGCC GCGTTCCACT GAGCGTCAGA    50

CCCC    54

( 2 ) INFORMATION FOR SEQ ID NO:14:

( i ) SEQUENCE CHARACTERISTICS:
    ( A ) LENGTH: 42
    ( B ) TYPE: nucleic acid
    ( C ) STRANDEDNESS: single
    ( D ) TOPOLOGY: linear ( i i ) MOLECULE TYPE: primer for pBR322 ori positions 2380-2404

( i i i ) HYPOTHETICAL: no ( x i ) SEQUENCE DESCRIPTION: SEQ ID NO:14:

GGCGGTCCTG TTTAAACGCT GCGCTCGGTC GTTCGGCTGC GG    42

( 2 ) INFORMATION FOR SEQ ID NO:15:

( i ) SEQUENCE CHARACTERISTICS:
    ( A ) LENGTH: 28
    ( B ) TYPE: nucleic acid
    ( C ) STRANDEDNESS: single
    ( D ) TOPOLOGY: linear ( i i ) MOLECULE TYPE: dialpha gene fragment ( i i i ) HYPOTHETICAL: no ( x i ) SEQUENCE DESCRIPTION: SEQ ID NO:15:

CAATTTCACA GGAAATTAAT TAATGCTG    28

( 2 ) INFORMATION FOR SEQ ID NO:16:

( i ) SEQUENCE CHARACTERISTICS:
    ( A ) LENGTH: 30
    ( B ) TYPE: nucleic acid
    ( C ) STRANDEDNESS: single
    ( D ) TOPOLOGY: linear ( i i ) MOLECULE TYPE: dialpha gene fragment ( i i i ) HYPOTHETICAL: no ( x i ) SEQUENCE DESCRIPTION: SEQ ID NO:16:

CAATTTCACT AAGGAGGTTA ATTAATGCTG    30

( 2 ) INFORMATION FOR SEQ ID NO:17:

( i ) SEQUENCE CHARACTERISTICS:
    ( A ) LENGTH: 29
    ( B ) TYPE: nucleic acid
    ( C ) STRANDEDNESS: single
    ( D ) TOPOLOGY: linear ( i i ) MOLECULE TYPE: beta gene fragment ( i i i ) HYPOTHETICAL: no (xi) SEQUENCE DESCRIPTION: SEQ ID NO:17:

TAAAGATCTA GAGGAAATAA TATATGCAC                                              29

(2) INFORMATION FOR SEQ ID NO:18:

(i) SEQUENCE CHARACTERISTICS:
       (A) LENGTH: 33
       (B) TYPE: nucleic acid
       (C) STRANDEDNESS: single
       (D) TOPOLOGY: linear (ii) MOLECULE TYPE: beta gene fragment (iii) HYPOTHETICAL: no (xi) SEQUENCE DESCRIPTION: SEQ ID NO:18:

TAATGATCTA GATAAGGAGG TAAATATATG CAC                                         33

(2) INFORMATION FOR SEQ ID NO:19:

(i) SEQUENCE CHARACTERISTICS:
       (A) LENGTH: 16
       (B) TYPE: nucleic acid
       (C) STRANDEDNESS: single
       (D) TOPOLOGY: linear (ii) MOLECULE TYPE: beta terminus (iii) HYPOTHETICAL: no (xi) SEQUENCE DESCRIPTION: SEQ ID NO:19:

CTCGCTCACT AATGAA                                                            16

(2) INFORMATION FOR SEQ ID NO:20:

(i) SEQUENCE CHARACTERISTICS:
       (A) LENGTH: 25
       (B) TYPE: nucleic acid
       (C) STRANDEDNESS: single
       (D) TOPOLOGY: linear (ii) MOLECULE TYPE: modified beta terminus (iii) HYPOTHETICAL: no (xi) SEQUENCE DESCRIPTION: SEQ ID NO:20:

CTCGCTCACA AATACCACTA ATGAA                                                  25